(12) United States Patent  (10) Patent No.: US 8,929,630 B2
Fu  (45) Date of Patent: Jan. 6, 2015

(54) SYSTEMS AND METHODS FOR ASSESSING IMAGES

(75) Inventor: Haoning Fu, Foster City, CA (US)

(73) Assignee: Life Technologies Corporation, Carlsbad, CA (US)

( * ) Notice: Subject to any disclaimer, the term of this patent is extended or adjusted under 35 U.S.C. 154(b) by 1141 days.

(21) Appl. No.: 12/748,158

(22) Filed: Mar. 26, 2010

(65) Prior Publication Data

US 2010/0246977 A1    Sep. 30, 2010

Related U.S. Application Data

(60) Provisional application No. 61/164,262, filed on Mar. 27, 2009.

(51) Int. Cl.
*G06K 9/00* (2006.01)
*G01N 21/64* (2006.01)

(52) U.S. Cl.
CPC .... *G01N 21/6456* (2013.01); *G01N 2021/6441* (2013.01); *G01N 21/6428* (2013.01)
USPC .......................................................... 382/129

(58) Field of Classification Search
USPC .................................................. 382/128–133
See application file for complete search history.

(56) References Cited

U.S. PATENT DOCUMENTS

| | | | |
|---|---|---|---|
| 5,846,729 A | 12/1998 | Wu et al. | |
| 6,043,506 A | 3/2000 | Heffelfinger et al. | |
| 7,039,889 B2* | 5/2006 | Takahashi et al. | 716/52 |
| 7,817,840 B2* | 10/2010 | Mattheakis et al. | 382/133 |
| 8,055,034 B2* | 11/2011 | Dube et al. | 382/128 |
| 2003/0215867 A1 | 11/2003 | Gulati | |
| 2005/0037406 A1* | 2/2005 | De La Torre-Bueno et al. | 435/6 |
| 2005/0153349 A1* | 7/2005 | Ghosh et al. | 435/6 |
| 2005/0234656 A1* | 10/2005 | Schwartz et al. | 702/20 |
| 2006/0050946 A1* | 3/2006 | Mitchison et al. | 382/133 |

(Continued)

FOREIGN PATENT DOCUMENTS

| | | |
|---|---|---|
| EP | 1450304 | 8/2004 |
| WO | WO-2010/111656 | 9/2010 |
| WO | WO 2010111656 A2 * | 9/2010 |

OTHER PUBLICATIONS

M-C De Cian; Andersen, A; J-Y Toullec; et al. "Isolated bacteriocyte cell suspensions from the hydrothermal-vent tubeworm *Riftia pachyptila*, a potent tool for cellular physiology in a chemoautotrophic symbiosis." Marine Biology142.1 (Jan. 2003): 141-151.*

(Continued)

*Primary Examiner* — Robert Sorey

(57) ABSTRACT

Disclosed are systems and methods for assessing images in applications such as microscopic scanning of a slide having light emitting objects. In certain embodiments, such scanning can involve objects such as sequencing beads disposed on the slide to facilitate biological analysis such as nucleic acid sequencing. Also disclosed are certain embodiments where images of light emitting objects are assessed for image quality so as to facilitate a feedback response such as a corrective action. In certain embodiments, such assessment and correction can be performed in real-time during the scanning process, and can include re-acquisition of the assessed image. Also disclosed are certain embodiments where such assessment and correction can be triggered dynamically during the scan, or before start of the scan, so as to enhance the scanning performance, including scanning time and throughput.

15 Claims, 31 Drawing Sheets

(56) References Cited

U.S. PATENT DOCUMENTS

| | | | |
|---|---|---|---|
| 2006/0292583 A1* | 12/2006 | Schneider et al. | 435/6 |
| 2007/0041624 A1* | 2/2007 | Cork et al. | 382/128 |
| 2007/0140540 A1* | 6/2007 | McLaren et al. | 382/128 |
| 2008/0003571 A1* | 1/2008 | McKernan et al. | 435/6 |
| 2008/0075380 A1* | 3/2008 | Dube et al. | 382/255 |
| 2008/0274905 A1* | 11/2008 | Greene | 506/4 |
| 2009/0061526 A1* | 3/2009 | Hong et al. | 436/94 |
| 2009/0262994 A1* | 10/2009 | Haussecker et al. | 382/128 |

OTHER PUBLICATIONS

PCT/US2010/028923 International Preliminary Report on Patentability Mailed Oct. 6, 2011, pp. 1-8.

PCT/US2010/028923 International Search Report Mailed Jan. 28, 2011, pp. 1-5.

PCT/US2010/028923 Written Opionion Mailed Jan. 28, 2011, pp. 1-6.

PCT/US11/028923 International Search Report mailed Jan. 28, 2011.

* cited by examiner

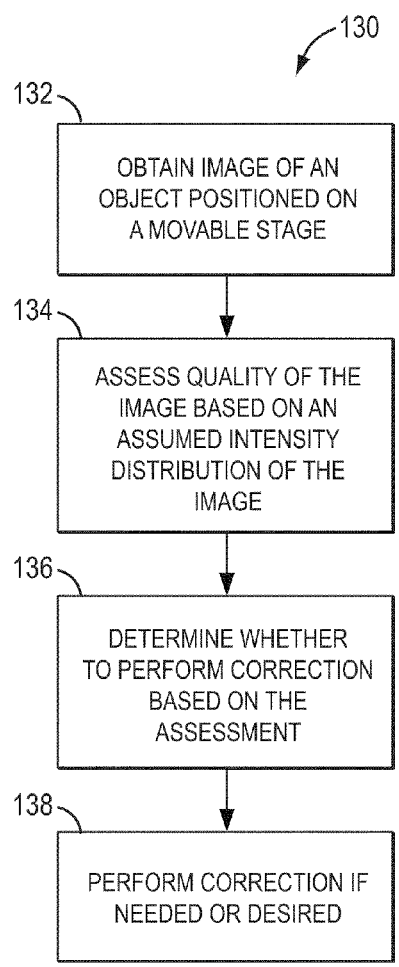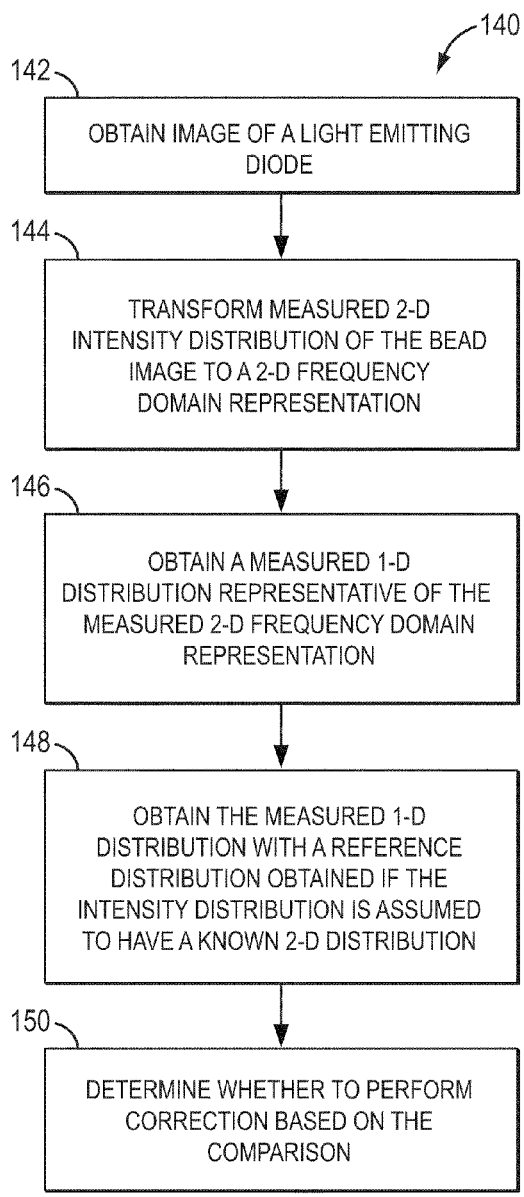
FIG. 4
FIG. 5

SYSTEMS AND METHODS FOR ASSESSING IMAGES

CROSS-REFERENCE TO RELATED APPLICATIONS

This application claims priority to U.S. Ser. No. 61/164,262, filed Mar. 27, 2009, the disclosure of which is hereby incorporated herein by reference in their entirety as if set forth fully herein.

BACKGROUND

1. Field

The present disclosure generally relates to the field of image processing, and more particularly, to systems and methods for performing image quality assessment and providing a feedback response based on the assessment.

2. Description of the Related Art

In many imaging applications such as microscopic resolution of a biological sample, multiple images can be obtained from different portions of the sample. As is usually the case, quality of such images is an important consideration.

There can arise various conditions that can affect the quality of one or more of the multiple images, or even blocks of such images. Thus, detecting such condition(s) can facilitate maintenance or improvement of quality of images; and the overall quality of the imaging result.

In many of such applications, speed of scanning or imaging competes against image quality performance. For example, a technique that emphasizes image quality can come at the expense of a lengthy acquisition time. In certain situations where the number of images obtained or scan area is relatively large, such lengthy time requirement may not be desirable, or even make the imaging or scanning process impractical. Thus, the efficiency of the image acquisition process can be an important consideration.

SUMMARY

In certain embodiments, the present disclosure relates to a nucleic acid sequencing system. The system can include a flow cell having a plurality of beads, where each bead can have one or more nucleic acid fragments attached thereto. The system can further include a plurality of dye labeled oligonucleotide probes configured to query sequence of at least a portion of the one or more nucleic acid fragments. The dye can be configured to emit a detectable signal when excited by excitation energy. The system can further include an imaging system configured to detect the detectable signal and form an image so as to allow sequencing of the at least a portion of the one or more nucleic acid fragments. The imaging system can include a focus system and an exposure system to facilitate formation of the image. The system can further include an assessment component configured to assess the image based on a comparison of a measured signal distribution of a bead in the image with a reference distribution.

In certain embodiments, the system can further include a correction component configured to induce correction of at least one condition, such as bad focus, bad exposure, or vibration, based on the image assessment. In certain embodiments, such assessment and correction can occur in substantially real time.

In certain embodiments, the present disclosure relates to a method for scanning a slide mounted to a stage and populated with sequencing probe particles. The method can include: (a) preparing the stage to allow movements of the stage to thereby allow imaging of a plurality of panels of sequencing probe particles on the slide, where the stage can be movable along a z-axis that is substantially parallel to an optical axis between the slide and an objective lens; (b) for a given panel in a group of panels, obtaining an image and assessing the image based on a comparison of a measured signal distribution of a sequencing probe particle with a reference distribution, and determining whether the image should be re-acquired based on the assessment; and (c) if re-acquirable, correcting a condition that contributed to degradation of the image and re-acquiring a new image after the correction.

In certain embodiments, the method can further include a step that can, prior to scanning of the group of panels in steps (b) and (c), determining whether the image assessment and re-acquisition should be performed for the group of panels. In certain embodiments, scanning the group of panels can be performed without steps (b) and (c) if determination is made that the image assessment and re-acquisition should not be performed for the group of panels.

In certain embodiments, the present disclosure relates to a method for scanning a slide mounted to a stage and populated with sequencing probe particles arranged in a plurality of panels, with the panels being arranged in a plurality of groups. The method can include: (a) preparing the stage to allow predetermined movements of the stage to thereby allow imaging of the plurality of panels of sequencing probe particles on the slide; (b) for a given group, obtaining, for each of a sample N panels in the given group, an image and assessing the image based on a comparison of a measured signal distribution with a reference distribution, and designating the panel as good or bad based on an assessment of the image; estimating a probability that ratio of the good panels to bad panels among the sample N panels is representative of an actual good-to-bad panel ratio among all panels in the given group; and determining whether to perform image assessment and image re-acquisition based on the assessment for all the panels during a full scan of the given group; and (c) repeating step (b) for other groups of the panels.

In certain embodiments, the present disclosure relates to a method for dynamically changing a scanning configuration during a scan of a slide, where the slide is populated with sequencing probe particles arranged in a plurality of sub-units, with the plurality of sub-units arranged in one or more units. The method can include obtaining an image of a sub-unit and assessing the image based on a comparison of a measured signal distribution of a sequencing probe particle with a reference distribution. The method can further include determining whether the sub-unit is a bad sub-unit based at least in part on the assessment. The method can further include aborting scanning of the unit in which the bad sub-unit belongs based at least in part on the sub-unit being a bad sub-unit.

In certain embodiments, the present disclosure relates to a method for assessing an image of a slide populated with a plurality of sequencing beads. The method can include obtaining an image having one or more sequencing beads that emit detectable signals, where at least some of the sequencing beads are capable of facilitating a plurality of ligation cycles. The method can further include evaluating the image by comparing a measured signal distribution of at least one sequencing bead with a reference distribution, with the comparison being performed at a range within the measured signal and reference distributions. The range can be selected based on one or more conditions of the sequencing beads.

In certain embodiments, the present disclosure relates to a method for focusing during scanning of a microscope slide mounted on a movable stage. The method includes obtaining an image of a portion of the slide. The method further includes assessing the image to determine whether the image is a bad image. If the image is determined to be bad, the method can predict what a new a focusing surface should be. The method further includes inducing movement of the stage based on the updated focusing surface.

In certain embodiments, the method can further include acquiring a new image after the stage movement. In certain embodiments, the inducing of movement is performed on-the-fly and prior to the assessment of next image.

In certain embodiments, the present teachings provide a nucleic acid sequencing system, comprising: a reaction chamber having a plurality features, each feature associated with one or more nucleic acid molecules; a plurality of labeled probes configured to emit detectable signals and used to query the sequence of at least a portion of said one or more nucleic acid molecules; an imaging system having a focus component and an exposure component configured to detect said detectable signals and form an image used in sequencing of said at least a portion of said one or more nucleic acid molecules; and an assessment component configured to assess a focus quality of said image based on a comparison of a measured signal distribution of a selected feature in said image with a reference signal distribution of the selected feature.

In certain embodiments, said reference signal distribution comprises a distribution associated with fluorescent emissions of said detectable signals from said feature.

In certain embodiments, said measured signal distribution comprises a 2-dimensional intensity distribution of said feature.

In certain embodiments, said reference signal distribution comprises a 2-dimensional Gaussian distribution.

In certain embodiments, said measured signal distribution and reference signal distribution comprise fast Fourier transforms (FFT) of said 2-dimensional intensity distribution and 2-dimensional Gaussian distribution, respectively.

In certain embodiments, said measured signal distribution and reference signal distribution comprise respective 1-dimensional representations of said FFTs of said 2-dimensional intensity distribution and 2-dimensional Gaussian distribution.

In certain embodiments, said 1-dimensional representation comprises a distribution of a plurality of average values, each average value being calculated from values obtained from an isocentric circle about a peak value of the corresponding 2-dimensional distribution.

In certain embodiments, said comparison comprises fitting of said 1-dimensional representation of said measured signal distribution to said 1-dimensional representation of said reference signal distribution.

In certain embodiments, said 1-dimensional representations of measured signal distribution and reference signal distribution are linearized and used in a linear fitting.

In certain embodiments, a correlation coefficient of said linear fitting provides an index of a quality of said image.

In certain embodiments, a correction component configured to induce correction of at least one condition based on said image assessment.

In certain embodiments, said at least one condition comprises said image being out of focus beyond a selected range.

In certain embodiments, said at least one condition comprises said image having an exposure beyond a selected range.

In certain embodiments, said at least one condition comprises vibrations affecting said image.

In certain embodiments, said reaction chamber includes a substrate with said plurality of features disposed thereon, said reaction chamber and imaging system being positionable with respect one another to permit scanning of portions of the substrate by the imaging system to thereby image said plurality of features.

In certain embodiments, said inducement of correction occurs in substantially real time.

In certain embodiments, said correction of at least one condition occurs prior to formation of the next image by said imaging system.

In certain embodiments, said next image comprises a re-acquired image, having said correction, of said one or more of said plurality of features.

In certain embodiments, said one or more nucleic acid molecules comprises template nucleic acid strands to be sequenced.

In certain embodiments, said plurality of probes comprise a plurality of oligonucleotide labeled probes.

In certain embodiments, a quality value is generated and output to a user reflecting the assessment of focus quality.

In certain embodiments, the present teachings provide a method for scanning a substrate mounted to a stage and populated with features to be sequenced, comprising: (a) preparing said stage to allow movements of said stage to thereby allow imaging of a plurality of panels of features on said substrate, said stage movable along a z-axis that is substantially parallel to an optical axis between said substrate and an objective lens; (b) for a given panel in a group of panels: obtaining an image and assessing said image based on a comparison of a measured signal distribution of a feature with a reference distribution; and determining whether said image should be re-acquired based on said assessment; and (c) if re-acquirable: correcting a condition that contributed to degradation of said image; and re-acquiring a new image after said correction.

In certain embodiments, said reference distribution comprises a distribution that is associated with emission of detectable signals from said feature.

In certain embodiments, said movements of said stage comprise a predetermined sequence of stage movements.

In certain embodiments, said method comprises repeating steps (b) and (c) for said selected group of panels.

In certain embodiments, said correction of said condition and said re-acquisition are performed by positioning said stage to a position corresponding to said assessed image.

In certain embodiments, said correction and re-acquisition are performed prior to said stage moving to a position corresponding to a panel that has not been imaged.

In certain embodiments, said stage movement to said assessed image position occurs after one movement of said stage from said assessed image position to another panel position.

In certain embodiments, said assessment occurs during said one movement.

In certain embodiments, said step (b) further comprises designating said given panel as a bad panel and storing information about said bad panel to facilitate said correction and re-acquisition.

In certain embodiments, said storing of information comprises filling a rescue queue so as to allow retrieval for said correction and re-acquisition.

In certain embodiments, said rescue queue comprises a first-in-first-out (FIFO) queue.

In certain embodiments, said condition comprises at least one of a bad focus, a bad exposure, or stage vibration.

In certain embodiments, said correction for said stage vibration comprises increasing a delay after stage movement.

In certain embodiments, said correction for said bad exposure comprises adjusting an auto exposure parameter.

In certain embodiments, said correction for said bad focus comprises: moving said stage along said z-axis so as to obtain a focus setting; and re-acquiring said new image at said focus setting.

In certain embodiments, said moving of the stage comprises moving said stage to a cached z value of said substrate at said given panel if a measured surface definition of said substrate about said given panel is collectively displaced from a corresponding cached surface definition, and to a measured z value of said slide at said given panel if said measured surface definition is not collectively displaced from said corresponding cached surface definition.

In certain embodiments, said measured surface definition of said substrate about said given panel is defined by a plurality of measured surface values at and about said given panel, each of said plurality of measured surface values obtained by via auto focus.

In certain embodiments, said plurality of measured surface values are obtained at said given panel and one or more of panels that preceded said given panel.

In certain embodiments, said measured surface is deemed to be collectively displaced from said corresponding cached surface if said surfaces are substantially parallel to each other and displaced along said z-direction.

In certain embodiments, said method further comprises updating said corresponding cached surface definition if said surfaces are not substantially parallel to each other.

In certain embodiments, said method further comprises determining whether said re-acquired image is acceptable based on an assessment of said re-acquired image.

In certain embodiments, said assessment comprises a comparison of a measured signal distribution with a reference distribution.

In certain embodiments, said method further comprises accounting the number of panels whose corresponding re-acquired images fail said assessment.

In certain embodiments, said method, further comprises terminating steps (b) and (c) for said group of panels if said number of failed panels exceed a selected value.

In certain embodiments, said selected value is chosen based at least in part on a statistical confidence level that said group of panels will likely include at least a selected number of bad panels, each of said bad panels either having failed assessment of re-acquired image or would fail assessment if its image was re-acquired.

In certain embodiments, said method further comprises, prior to scanning of said group of panels in steps (b) and (c), determining whether said image assessment and re-acquisition should be performed for said group of panels.

In certain embodiments, said scanning said group of panels is performed without steps (b) and (c) if determination is made that said image assessment and re-acquisition should not be performed for said group of panels.

In certain embodiments, said determination comprises sampling and assessing a selected number of panels in said group.

In certain embodiments, said selected number is chosen based at least in part on a statistical confidence level that said group of panels will likely include at least a selected number of bad panels, each of said bad panels likely to fail an assessment if its image was re-acquired.

In certain embodiments, said sampling comprises a substantially random sampling.

In certain embodiments, said sampling comprises measurement of pre-scan signals that are different than said detectable signals in step (b).

In certain embodiments, said pre-scan signals comprise non-fluorescent signals.

In certain embodiments, the present teachings comprise a method for scanning a substrate mounted to a stage and populated with features arranged in a plurality of panels, said panels further arranged in a plurality of groups, said method comprising: (a) preparing said stage to allow predetermined movements of said stage to thereby allow imaging of said plurality of panels of features on said substrate; (b) for a given group: for each of a sample N panels in said given group, obtaining an image and assessing said image based on a comparison of a measured signal distribution with a reference distribution, and designating said panel as good or bad based on an assessment of said image; estimating a probability that ratio of said good panels to bad panels among said sample N panels is representative of an actual good-to-bad panel ratio among all panels in said given group; and determining whether to perform image assessment and image re-acquisition based on said assessment for all said panels during a full scan of said given group; and (c) repeating step (b) for other groups of said panels.

In certain embodiments, said image corresponding to said sample panel comprises an image of one or more channels emitting substantially non-fluorescent light.

In certain embodiments, said steps (b) and (c) are performed prior to said full scan of groups of panels.

In certain embodiments, the present teachings comprise a method for dynamically changing a scanning configuration during a scan of a slide, said slide populated with features arranged in a plurality of sub-units, said plurality of sub-units arranged in one or more units, said method comprising: obtaining an image of a sub-unit and assessing said image based on a comparison of a measured signal distribution of a feature with a reference distribution; determining whether said sub-unit is a bad sub-unit based at least in part on said assessment; and aborting scanning of the unit in which said bad sub-unit belongs based at least in part on said sub-unit being a bad sub-unit.

In certain embodiments, said aborting occurs when said bad sub-unit increases a count of bad sub-units in said unit beyond a threshold amount.

In certain embodiments, the present teachings comprise a method for assessing an image of a substrate populated with a plurality of features, comprising: obtaining an image having one or more features that emit detectable signals, at least some of said features associated with nucleic acid probes; evaluating said image by comparing a measured signal distribution of at least one nucleic acid template molecule with a reference distribution, said comparison being performed at a range within said measured signal and reference distributions; wherein said range is selected based on one or more conditions of said nucleic acid probes.

In certain embodiments, said range comprises a 1-dimensional range.

In certain embodiments, said 1-dimensional range comprises a range in a frequency representation of said measured and reference distributions.

In certain embodiments, said 1-dimensional frequency range comprises a range where said frequency representation is or approximately linear.

In certain embodiments, said range is selected so that when said ligation cycle is at a relatively higher number, upper limit of said frequency range is reduced to account for a shift in said approximately linear portion.

In certain embodiments, said range is selected so that when the density of nucleic acid probes is at a relatively higher number, either or both of lower and upper limits of said frequency range is changed so as to maintain said approximately linear property of said frequency range.

BRIEF DESCRIPTION OF THE DRAWINGS

The skilled artisan will understand that the drawings, described below, are for illustration purposes only. The drawings are not intended to limit the scope of the present teachings in any way

FIG. 4 shows an example process for assessing an image based on a comparison of a measured distribution with a reference distribution, and if needed or desired, performing a correction based on the assessment;

FIG. 5 shows that in certain embodiments, assessment of an image can include transformation of a 2-dimensional intensity distribution of detected light from a probe particle into a frequency domain representation so as to allow comparison with a reference distribution;

These and other aspects, advantages, and novel features of the present teachings will become apparent upon reading the following detailed description and upon reference to the accompanying drawings. In the drawings, similar elements have similar reference numerals.

DETAILED DESCRIPTION OF CERTAIN EMBODIMENTS

Figure 1:
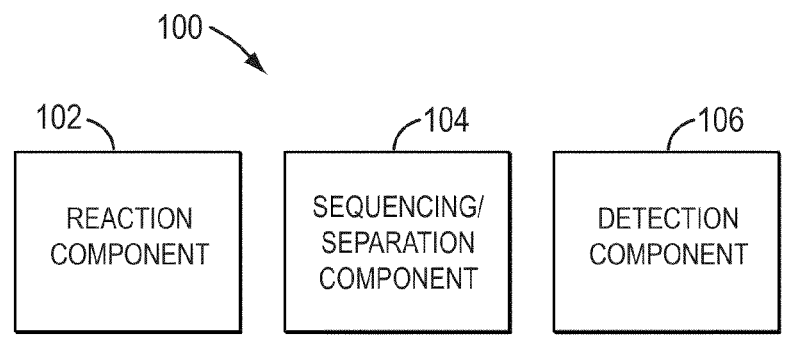
FIG. 1 shows a block diagram of one embodiment of a system components associated with analysis of biological materials or processes.

The use of "or" herein means "and/or" unless stated otherwise or where the use of "and/or" is clearly inappropriate. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of." It should also be understood that in some embodiments the order of steps or order for performing certain actions is immaterial so long as the present teachings remain operable. Moreover, in some embodiments two or more steps or actions can be conducted simultaneously.

Throughout the specification, reference is made to biological instruments and/or samples. It should be understood that the biological analysis instruments in accordance with the present teachings may be configured to perform multiple processes on various amounts of samples serially, simultaneously or otherwise. Further, differing types of sample can be processed simultaneously. Thus, when reference is made to a sample being provided in a reaction chamber, it should be understood that the term can refer to either a single type of sample in a single amount, multiple amounts of a single type of sample, and/or multiple amounts of differing types of sample. The term also can be used to refer to a bulk amount of substance placed in the reaction chamber. Further, in its broadest sense, the term sample can include the various reagents, etc. that are introduced to the chamber to perform an analysis or other process therein.

In various exemplary embodiments described herein, reaction chambers may include but are not limited to flow cells. Such reaction chambers can be configured to contain or flow reagents into a desired region to react with for example multiple template nucleic acids simultaneously in order to perform sequencing of the template nucleic acids residing on or arranged near the substrate at discrete locations. Examples of various substrates which may be used to secure, hold, or contain nucleic acid templates and methods of reacting nucleic acid templates associated with such substrates can be found in WO 2006/084132, which published Aug. 10, 2006, entitled "REAGENTS, METHODS, AND LIBRARIES FOR BEAD-BASED SEQUENCING," and is incorporated herein by reference in its entirety.

Similarly, the aforementioned teachings describe various approaches to nucleic acid sequencing, however, it will be appreciated that the system and methods described herein may be readily adapted to other sequencing methods or approaches without departing from the scope or spirit of the invention. Similarly, the present teachings may be adapted to other analytical methods outside of nucleic acid sequencing including but not limited to protein or amino-acid analysis, nucleic acid amplification including for example PCR (including end-point and real-time applications), micro-array analysis of proteins, nucleic acids, and/or other biological molecules, and cellular analysis. Additionally, the system and methods described herein my be adapted for use in other contexts including imaging and auto-focus applications such as those implemented for resolving small or microscopic features.

The term "nucleic acid" can be used interchangeably with "polynucleotide" or "oligonucleotide" and can include single-stranded or double-stranded polymers of nucleotide monomers, including 2'-deoxyribonucleotides (DNA) and ribonucleotides (RNA) linked by internucleotide phosphodiester bond linkages, or internucleotide analogs, and associated counter ions, for example, H+, NH4+, trialkylammonium, Mg2+, Na+ and the like. A polynucleotide can be composed entirely of deoxyribonucleotides, entirely of ribonucleotides, or chimeric mixtures thereof. Polynucleotides can be comprised of nucleobase and sugar analogs. Polynucleotides typically range in size from a few monomeric units, for example, 5-40 when they are frequently referred to in the art as oligonucleotides, to several thousands of monomeric nucleotide units. Unless denoted otherwise, whenever a polynucleotide sequence is represented, it will be understood that the nucleosides are in 5' to 3' order from left to right and that "A" denotes deoxyadenosine, "C" denotes deoxycytidine, "G" denotes deoxyguanosine, and "T" denotes thymidine, unless otherwise noted. A labeled polynucleotide can comprise modification at the 5' terminus, 3' terminus, a nucleobase, an internucleotide linkage, a sugar, amino, sulfide, hydroxyl, or carboxyl. See, for example, U.S. Pat. No. 6,316,610 B2, which issued Nov. 13, 2001 and is entitled "LABELLED OLIGONUCLEOTIDES SYNTHESIZED ON SOLID SUPPORTS," which is incorporated herein by reference. Similarly, other modifications can be made at the indicated sites as deemed appropriate.

The term "reagent" should be understood to mean any reaction component that in any way affects how a desired reaction can proceed or be analyzed. The reagent can comprise a reactive or non-reactive component. It is not necessary for the reagent to participate in the reaction. The reagent can be a recoverable component comprising for example, a solvent and/or a catalyst. The reagent can comprise a promoter, accelerant, or retardant that is not necessary for a reaction but affects the reaction, for example, affects the rate of the reaction. A reagent can comprise, for example, one member of a binding pair, a buffer, or a nucleic acid strand or oligonucleotide that can hybridize to another nucleic acid strand or oligonucleotide. The term "reagent" is used synonymous with the term "reaction component."

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

Reference will now be made in detail to various exemplary embodiments of the present teachings, examples of which are illustrated in the accompanying drawings. Wherever possible, the same reference numbers will be used throughout the drawings to refer to the same or like parts.

The present disclosure generally relates to systems and methods for imaging signals associated with analytical devices such as biological analysis devices. By way of a non-limiting example, such biological analysis devices can include a genetic analysis device used for nucleic acid sequencing.

In many of such devices, excitation energy such as light or electromagnetic radiation is provided to a detection zone where features, areas or particles of interest contain or are associated with nucleic acid fragments tagged with detectable labels such as fluorescent labels. Such excitation of the tagged labels results in detectable signals (such as fluorescent light) being emitted and detected, thereby allowing characterization of, for example, a sequence of a nucleic acid sample.

In many such devices, the detectable signals are collected and registered by an imaging detector such as a charge-coupled-device (CCD) or a complementary-metal-oxide-semiconductor (CMOS). Generally, accurate imaging of the signals from the tags, areas, and/or particles or features of interest is an important consideration. By way of non-limiting examples, proper focus, proper exposure, and stability of the object being imaged are conditions that can contribute to the overall quality of the image. Degradation of one or more of such conditions can adversely affect the quality of the image, and thereby can degrade qualitative or quantitative results from the analysis. Thus, it is desirable to be able to detect, and correct if needed, such conditions in an efficient manner.

In certain situations, the targets of interest can include nucleic acid strands or fragments (such as fluorescently tagged base molecules) used in a sequencing process. In certain embodiments, such fragments can be selectively attached, secured, or retained to features, particles or substrates such as microparticles or beads that are disposed on a surface such as a slide, channel, or reaction area. In certain embodiments, such selective attachment of the fragments can be done in connection with a sample strand that is being sequenced. Determining what bases are present, and in what order, resolves the sequence of the nucleic acid sample strands.

In such an example configuration, it is desirable to have the features or objects of interest be provided with a stable platform and imaged with, for example, proper focus, high contrast, and proper exposure, so as to allow signal identification and/or base calling results with high precision.

In certain situations, high precision may not be as useful or practical if the time required to achieve such results is too lengthy. This is especially true in situations where images are obtained for many different locations on a substrate (e.g. slide). If the number of such different locations is large, an increase in acquisition time of a given image can result in an overall change in analysis time that can be roughly approximated as the number of images times the relative increase or decrease.

In certain embodiments, various features of the present disclosures can allow detection of conditions such as bad focus, bad exposure, instability in the substrate platform, or any combination thereof. As disclosed herein, such detection can be achieved in a relatively quick and efficient manner.

In certain embodiments, detection of such example conditions can be followed by one or more actions. In certain embodiments, such actions can include corrections that can be achieved in real or substantially real time on an image by image basis. In certain embodiments, such actions can include a more global determination—for example, how and/or when a scan or imaging should be performed.

Various non-limiting examples are described below in reference to the drawings.

FIG. 1 shows an example schematic diagram for a biological analyzer 100 capable of characterizing (e.g., for example analysis of sample sequence/composition or sample/fragment analysis) biological samples (such as nucleic acid samples) or processes. In various embodiments, the analyzer 100 may include one or more components or devices that can be used for labeling and identification of the sample and may provide features for performing sequence analysis. In certain embodiments, the various components of the analyzer 100 can include separate components or a singular integrated system. The present disclosure may be applied to both automatic and semi-automatic sequence analysis systems as well as to methodologies wherein some of the sequence analysis operations are manually performed. Additionally, systems and methods described herein may be applied to other biological analysis platforms to improve the overall quality of the imaging and analysis.

In various embodiments, the methods and systems of the present disclosure may be applied to numerous different types and classes of photo and signal detection methodologies/optics and are not necessarily limited to CCD or CMOS based detectors. Additionally, although various embodiments of the present disclosure are described in the context of sequence analysis, these methods may be readily adapted to other devices/instrumentation and used for purposes other than biological analysis.

In various embodiments, the methods and systems of the present disclosure may be applied to numerous different types and classes of signal detection/label excitation methodologies and are not necessarily limited to fluorescent-based excitation systems.

In the context of sequence analysis, the example sequence analyzer 100 may include a reaction component 102 wherein amplification or reaction sequencing (for example, through fluorescent label incorporation by a polymerase or ligase) of various constituent molecules contained in the sample is performed. Using these techniques, a label or tag, such as a fluorescent label or tag may be introduced into the sample resulting in a detectable species that may be used to discern the nucleic acid sequence of the sample.

In certain embodiments, the reaction component 102 can be used to process nucleic acid strands that are anchored to a substrate of particle. Many such strands can be attached to different substrates or particles and can be further deposited on or attached to a slide or other substrate.

The analyzer 100 can include a sequencing or separation component 104. In certain embodiments, the labeled fragments may be subjected to a separation operation using a component 104. In certain embodiments, the component 104 can separate different labeled fragments and provide preferential binding of different targets/fragments to their respective probes.

In certain embodiments, the component 104 can include one or more processes where detectable (for example dye labeled) probes query, and if matching attach to, the nucleic acid strands anchored to the features, microparticles or substrate. In certain embodiments, such probing/matching can incorporate a ligation or polymerization process to allow sequential interrogating of the bases of the nucleic acid strand to resolve its sequence.

In certain embodiments, a detector component 106 can be configured to detect and facilitate identification of various sizes or differential compositions for the fragments based on the presence of the incorporated label or tag. In one example embodiment, fragment detection may be performed by generation of a detectable signal produced by a fluorescent label that is excited by an excitation source (e.g. a laser or arc lamp) tuned to the label's absorption wavelength. Energy absorbed by the label results in a fluorescence emission that corresponds to a signal measured for each fragment, molecule, or base of interest.

In certain embodiments, the detection component 106 can be configured to detect and measure signals from dye labeled nucleic acid fragments anchored to a substrate or microparticle. Such detection of the fragments can allow determination of the sequence by resolving the type of label incorporated into the fragment.

Figure 2:
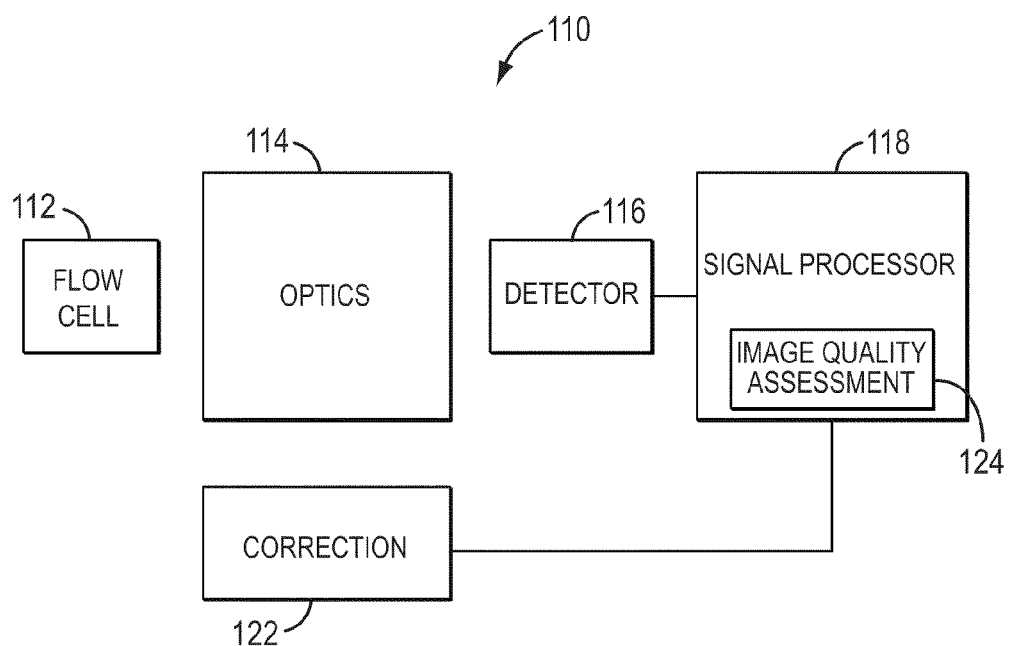
FIG. 2 shows an example system configured to perform an exemplary nucleic acid sequencing analysis, where the system can include an image quality assessment component and a correction component that can facilitate enhancement of quality and/or efficiency of image acquisition.

FIG. 2 shows an example detection configuration 110 where various components of the detector 106 (FIG. 1) may be used to acquire the signal associated with one or more labeled fragments or probes present in a detection zone 112. As previously indicated, the labeled fragments or probes in the detection zone 112 may be associated with discrete areas or microparticles which may be resolved by measuring the quantity of fluorescence or emitted energy generated when the fragments are subjected to excitation energy of appropriate wavelength and intensity. In certain embodiments, such excitation energy can be provided by an energy source such as an LED, laser or arc lamp or other source.

In certain embodiments, the energy emissions produced by the labeled sample/fragments in the detection zone 112 may be detected using a detector 116 and associated optics/filters. The detector 116 may comprise for example a CCD or a CMOS based detector. In certain embodiments, such detector 116 can have a plurality of energy detecting elements (e.g., pixels) that capture at least a portion of the emitted energy from the labeled fragments.

In certain embodiments, the detection zone 112 can include or be part of sample chamber, a flow cell, or other substrate where nucleic acid sequencing processes take place. In certain embodiments, such a sample chamber, flow cell or substrate can include a slide or surface that provides a mounting region or attachment for one or more nucleic acid strands (e.g., via beads, microparticles, substrate interactions etc.). In such configurations, images can be obtained via an optics component 114, and such images can be captured by the detector 116.

In certain embodiments, a signal processor 118 can be configured to perform signal acquisition operations to acquire the signal generated by the detector 116 in response to the signals from the detection zone 112.

In various embodiments, some of the information that may be determined through signal resolution and sample identification may include determination of the relative abundance or quantity of each sample/fragment/probe population. Evaluation of the signals may further be used to determine the sequence or composition of the sample using various known base sequence resolution techniques. It will further be appreciated by one of skill in the art that one or more signal distributions may represent one or more nucleic acid fragments for which the relative abundance and/or composition of each fragment may be evaluated. Such analysis may be based, at least in part, upon the determination of the type of signal, relative area of an associated peak in the signal distribution of the signal and/or the location of the signal. The present disclosure may therefore be integrated into existing analysis approaches to facilitate signal evaluation and subsequent operations typically associated with sequence analysis.

In various embodiments, the analysis of the signal representative of the aforementioned example data may be advantageously performed by the signal processor 118. The signal processor 118 may further be configured to operate in conjunction with one or more processors. The signal processor's components may include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables. Furthermore, the signal processor 118 may output a processed signal or analysis results to other devices or instrumentation where further processing may take place.

In certain embodiments, the processor 118 can include a component 124 that provides an image quality assessment. Examples of such assessment are described below in greater detail.

In certain embodiments, the detection configuration 110 can include a component 122 that induces and/or provides a correction in response to the image quality assessment. Examples of such correction are described below in greater detail.

Figure 3:
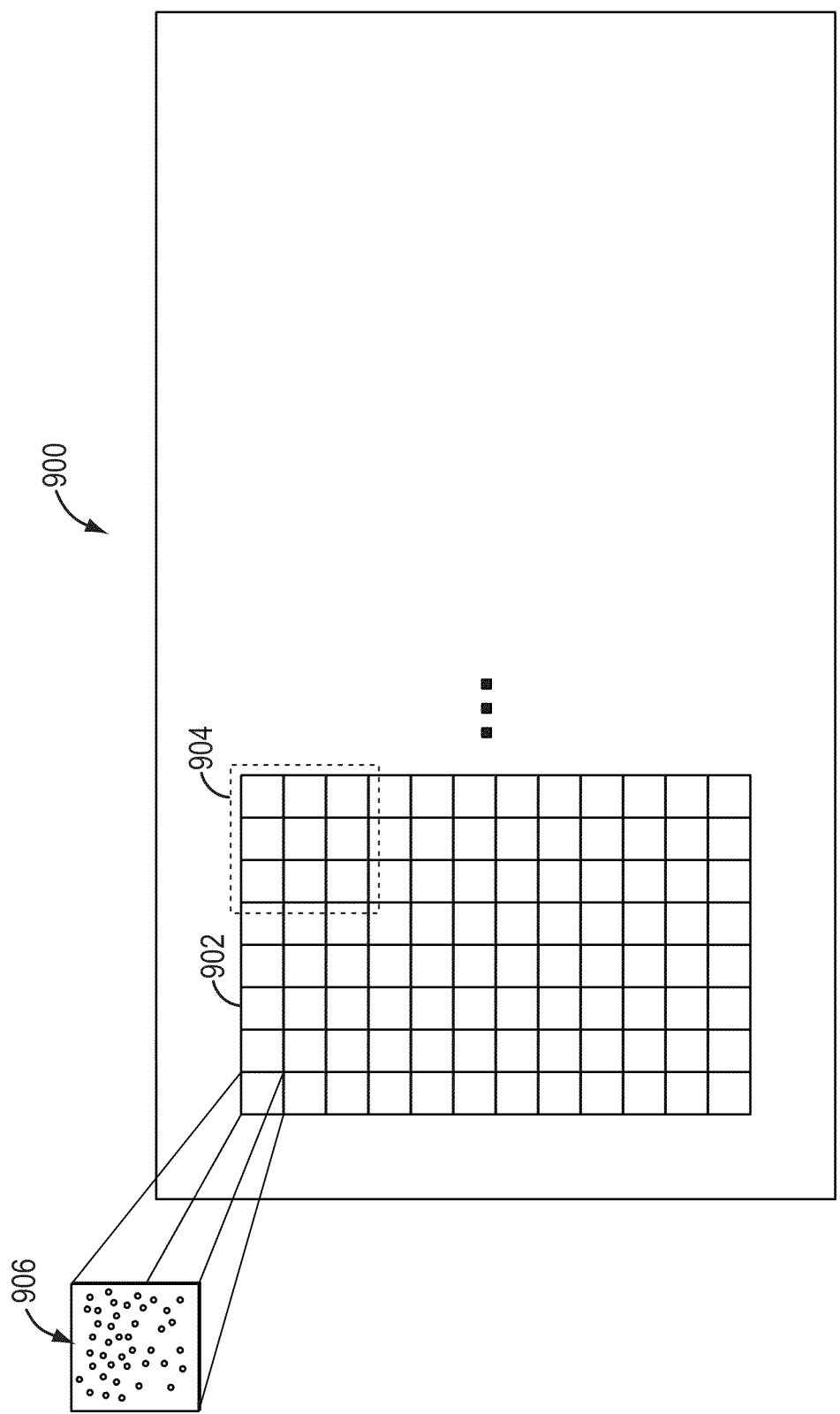
FIG. 3 shows an example slide or substrate adapted for use with the example analysis of FIG. 2, where the slide can be populated with probe species such as sequencing beads or particles.

For the purpose of description, an example substrate or slide 900 is depicted in FIG. 3. As described herein, such a slide can be part of a detection zone such as a flow cell or reaction chamber. The example slide 900 can have disposed on its surface a plurality of light or signal emitting elements or particles 906. In certain embodiments, such elements or particles can be labeled probe particles that query nucleic acid strands being sequenced (that, for example, can be immobilized to the slide via the microparticles or attached directly thereto). In certain embodiments, such particles comprise fluorescent dye labeled fragments being detected and measured so as to allow the sequencing of the nucleic acid strands.

In various embodiments, the signal-emitting portion (such as a fluorophore) itself, a particle having such signal-emitting label, or an assembly of particles or molecules having one or more such signal-emitting label(s) can be sufficiently small such that signal emission can be approximated as arising from a point source or localized area when focused properly. By way of a non-limiting example, the light-emitting particle 906 that includes a bead/nucleic acid strand/labeled probe particle assembly can be approximated as a point source when imaged by the detector.

In certain embodiments, a plurality of signal-emitting particles 906 can be grouped into a panel 902; and such grouping can be for the purpose of imaging and/or be based on some functional purpose. In certain embodiments, the slide 900 can be imaged by scanning the various panels 902 and collecting signals arising from each panel.

In certain embodiments, the panels 902 can be organized into one or more higher groups 904; and such grouping can be for the purpose of imaging and/or be based on some functional purpose. For the purpose of description herein, a group of panels 902 is sometimes referred to as a spot.

In certain embodiments, the example slide 900 can be mounted on a stage so as to allow various movements for focusing, scanning, and the like. It will be understood by one of ordinary skill in the art that such movements can be effectuated in known manners. For the purpose of description herein, it will be understood that Z-direction may be associated with focusing, and lateral XY-directions maybe associated with scanning.

The exemplary imaging approach can be implemented in an analysis system such as Applied Biosystem's SOLiD system for nucleic acid sequencing applications. While some of the example configurations and data are discussed herein in the context of the example SOLiD system, it will be understood that various concepts and techniques can also be implemented in other contexts, instruments, and applications as well.

FIG. 4 shows that in certain embodiments, a process 130 can be implemented. In a process block 132, an image of an object positioned on a movable stage can be obtained. In a process block 134, quality of the image can be assessed based at least in part on an assumed intensity distribution of the image. In a process block 136, the process 136 can determine whether to perform a correction based at least in part on the assessment. In certain embodiments, the process 138 can further include a process block 138 where the correction can be performed if determined to be needed or desired.

In certain embodiments, the object or feature being imaged (e.g., in the process block 132) can have a relatively small dimension that allows approximation of light or signal emission therefrom as a point source or a point-like or localized source. In certain embodiments, such an object can be a sequencing bead or particle having one or more nucleic acid strands attached thereto, where one or more of such strands have attached to it, or attached via a probe particle, a fluorophore. Similarly the object can be associated with a substrate surface and not necessarily a bead or microparticle.

In certain embodiments, the object being imaged can be detected by emission of fluorescent light, white light, or any other detectable signals. As described herein, at least some of the various features and techniques described herein are not limited to the frequency of light (e.g., can be fluorescent light or white light) or other electromagnetic signal.

FIG. 5 shows a process 140 that can be a more specific example of a portion of the process 130 of FIG. 4. In a process block 142, an image of a signal emitting object or feature can be obtained. In certain embodiments, such an image can include or feature information used to generate a two-dimensional intensity distribution of the object. In a process block 144, the measured two-dimensional intensity distribution of the object or feature can be transformed into a two-dimensional frequency domain representation. In certain embodiments, such transformation can be achieved by Fourier transform. In a process block 146, a one-dimensional representation of the measured two-dimensional frequency domain representation can be obtained. An example of such one-dimensional representation is described below in greater detail. In a process block 148, the measured one-dimensional representation can be compared with a similar reference distribution. In certain embodiments, such reference distribution can be obtained by assuming that the intensity distribution has, or can be approximated by, a known distribution. Examples of such reference distributions are described below in greater detail. In a process block 150, the process 140 can determine whether to perform a correction based at least in part on the comparison.

Figure 6:
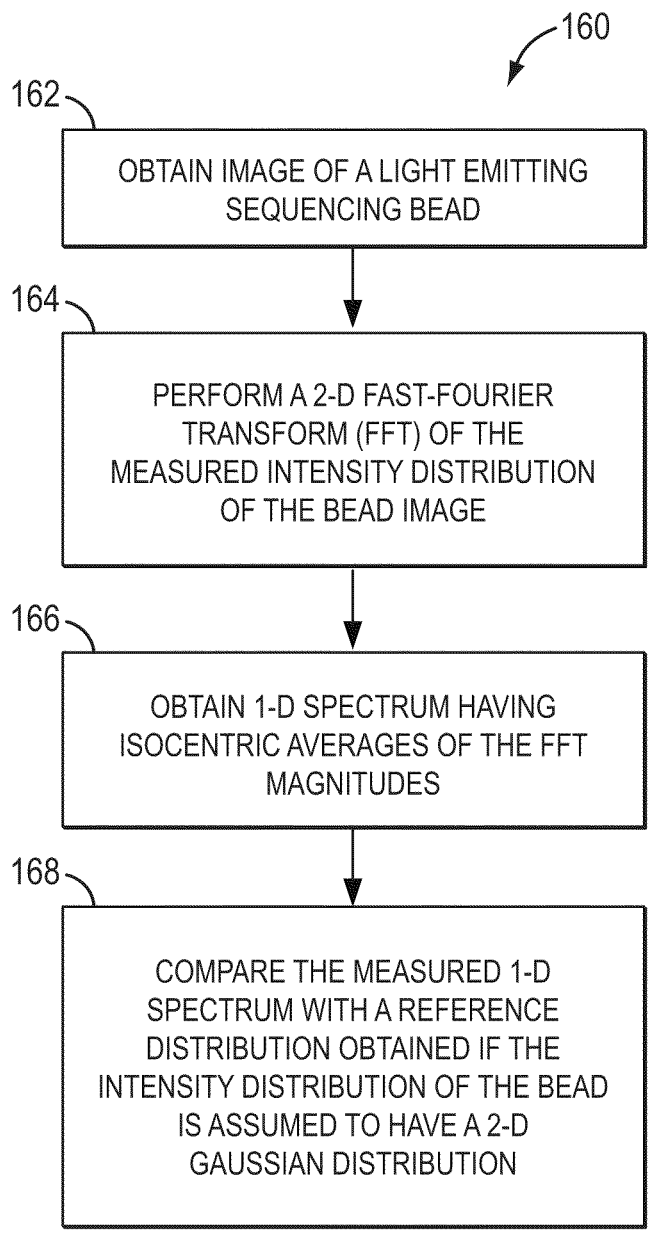
FIG. 6 shows an example of the assessment process of FIG. 5, where the reference distribution is selected to be a Gaussian distribution.

FIG. 6 shows a process 160 that can be a more specific example of a portion of the process 140 of FIG. 5. In a process block 162, an image of a signal emitting object or feature can be obtained. In a process block 164, a two-dimensional fast Fourier transform (FFT) can be applied to the measured two-dimensional intensity distribution obtained from the image, to provide the two-dimensional frequency representation. In a process block 166, a one-dimensional spectrum having isocentric averages of the FFT magnitudes can be obtained to provide the measured one-dimensional representation. In a process block 168, the measured one-dimensional isocentric-average spectrum can be compared to a similar reference spectrum. In certain embodiments, such reference spectrum can be obtained if the intensity distribution of the object is assumed to have a two-dimensional Gaussian distribution.

Figure 7A:
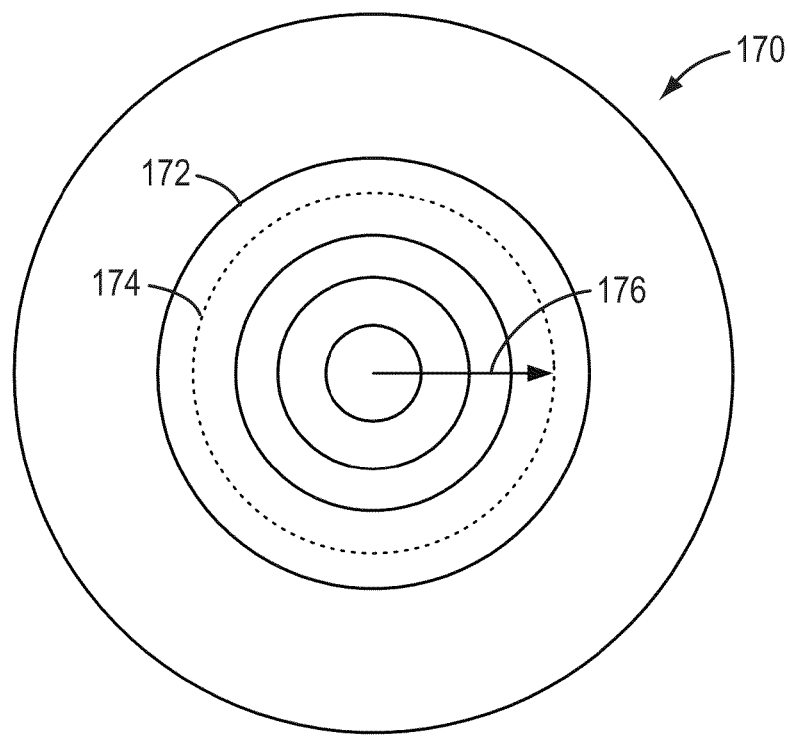
FIGS. 7A and 7B show by examples how a two-dimensional distribution can be represented as a one-dimensional distribution.
Figure 7B:
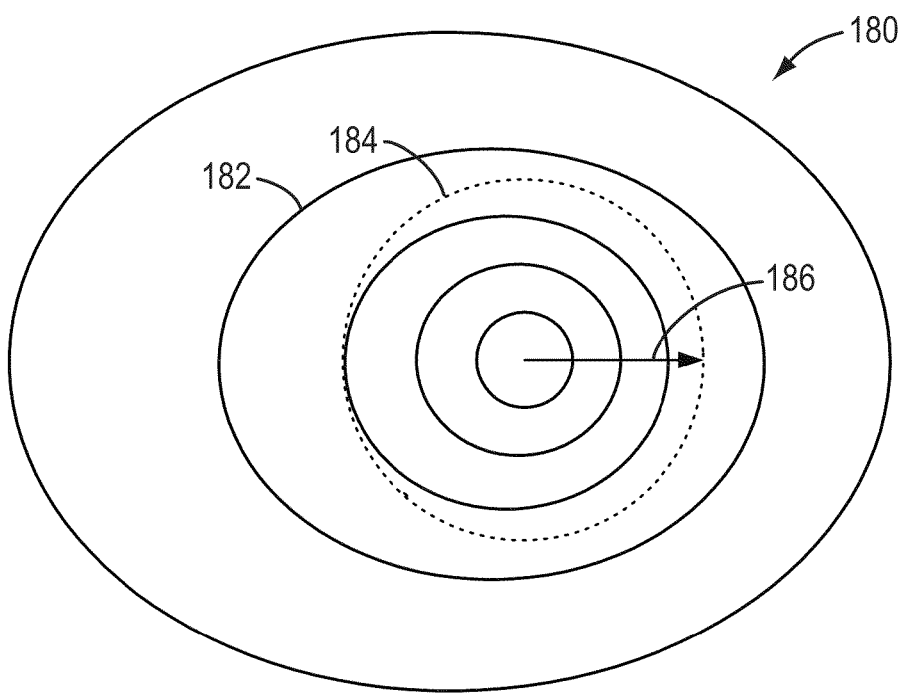

FIGS. 7A and 7B show by example how the one-dimensional isocentric-average spectrum can be obtained and used to distinguish a symmetric two-dimensional distribution (e.g., Gaussian distribution) from an asymmetric distribution. In certain situations, one or more conditions such as bad or non-optimal focus, bad or non-optimal exposure, and/or vibration can result in bead or feature images having distributions that deviate (such as asymmetry) from an ideal distribution such as a Gaussian.

In FIG. 7A, a contour plot of an example symmetric distribution 170 is depicted with a plurality of example contour lines 172. Such a distribution can be, for example, the two-dimensional frequency domain representation of the intensity distribution.

As shown in FIG. 7A, a circle 174 about some center (e.g., the peak location) can define isocentric locations about the center. Obtaining an average value of the isocentric circle 174 can provide a single value associated with a one-dimensional parameter (depicted as an arrow 176). For example, the average value can be obtained by sampling values at azimuthal intervals along the isocentric circle 174.

In the example symmetric two-dimensional distribution 170, the values of the isocentric circle 174 are substantially the same due to symmetry; thus, the one-dimensional spectrum will be highly representative of the two-dimensional distribution 170. If the two-dimensional distribution 170 is an ideal Gaussian, then the one-dimensional isocentric-average spectrum will also be an ideal one-dimensional Gaussian distribution.

FIG. 7B shows an example asymmetric two-dimensional distribution 180 depicted with a plurality of example contour lines 182. An example isocentric circle 184 is also depicted so as to allow obtaining of a single value associated with a one-dimensional parameter (depicted as an arrow 186). If an average value is obtained by sampling values at azimuthal intervals along the isocentric circle 184, one can see that values are different along the circle 184 due to asymmetry. Thus, one-dimensional isocentric-average spectrum will deviate from that of an ideal one-dimensional Gaussian distribution.

In certain embodiments, comparison of a one-dimensional isocentric-average spectrum with an ideal one-dimensional Gaussian distribution can be performed based on a linearized form of the Gaussian. For example, suppose that $|fft|=A\exp(Bu^2)$ represents the one-dimensional isocentric-average representation of a fast Fourier transform of a symmetric intensity distribution $I(r)=C\exp(Dr^2)$, where u represents the frequency domain variable and $r^2=x^2+y^2$. For the purpose of description, the Gaussian distributions are assumed to be centered about the origin. However, use of general forms of Gaussians (e.g., non-zero center) does not alter the underlying concepts of the present disclosure. The form |fft|=Aexp(Bu2) can be linearized as $$\log(|fft|) = Bu2 + \log A \qquad \text{Eq. 1}$$

so that log(|fft|) is proportional to u2.

In certain embodiments, a measured intensity distribution can be fast Fourier transformed and collapsed into the one-dimensional spectrum |fft|. Such measured spectrum can then be fitted between log(|fft|) and u2, and the degree of linearity (e.g., correlation coefficient) can provide a measure of deviation of the measured intensity distribution from that of the ideal reference distribution such as a Gaussian. Various examples of such one-dimensional spectra and degrees of linearity are described below in greater detail. As discussed herein, conditions such as bad or non-optimal focus, bad or non-optimal exposure, and/or vibration can result in decrease in degree of linearity, thereby allowing detection of such conditions. It will be understood that focus, exposure, and vibration are example conditions; and that other conditions can also contribute to decrease in image quality.

It will be understood that the foregoing technique of collapsing a two-dimensional distribution into a one-dimensional representation via the isocentric-average spectrum is a non-limiting example. There can be other forms of one-dimensional representation that can provide similar functionality as that of the example isocentric-averaging method.

It will also be understood that while the two-dimensional distributions are discussed in the context of Gaussians, other functions and forms can provide reference representations. Functions such as log of Gaussian, flat top kernels, and binormal are some non-limiting examples of reference distributions. In certain situations, one can even use an arbitrary probability density function that can be measured from a given instrument and represented as an array.

Figure 8:
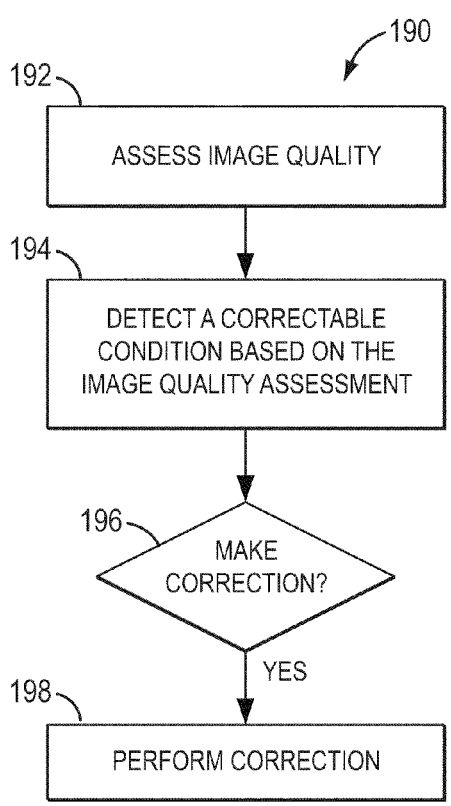
FIG. 8 shows an example process for determining whether to correct a detected condition based on the image quality assessment.

FIG. 8 shows one embodiment of a process 190 that can facilitate detection of one or more conditions based on assessment of an image. In a process block 192, image quality can be assessed. In certain embodiments, such assessment can include FFT and linear line fitting as describe herein by way of example. In a process block 194, a correctable condition can be detected based at least in part on the image quality assessment. In a decision block 196, the process 190 can determine whether a correction should be made based on the detection of a correctable condition. If the answer is "Yes," then the process 190 can induce or perform the correction in a process block 198.

Figure 9:
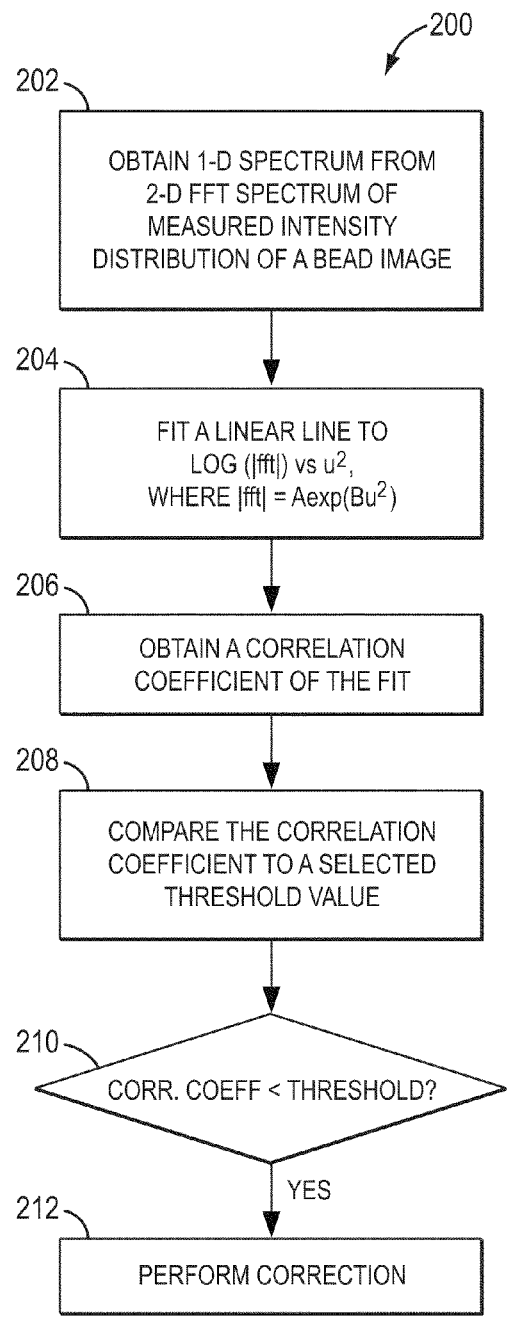
FIG. 9 shows an example of the process of FIG. 8, where a measure of linearity of the example one-dimensional frequency space representation can indicate quality of an image of an object such as a sequencing bead or particle.

FIG. 9 shows a more specific process 200 that can be an example of the process 190 of FIG. 8. In a process block 202, a one-dimensional spectrum can be obtained from a two-dimensional FFT spectrum of a measured intensity distribution of a bead or feature image. In a process block 204, a linear line can be fit to a set of values corresponding to log(|fft|) versus u2, where |fft|=Aexp(Bu2) is the one-dimensional representation of the two-dimensional FFT spectrum. In a process block 206, a correlation coefficient value can be obtained from the fit. In a process block 208, the correlation coefficient value can be compared to a selected threshold value. In a decision block 210, the process 200 can determine whether, for example, the correlation coefficient is less than the threshold value. If the answer is "Yes," then the process 200 can induce or perform the corresponding correction in a process block 212.

FIGS. 10-16 show examples of measurements that can allow detection of one or more conditions that are generally undesirable when imaging the slide. Such conditions can include, for example, bad or non-optimal focus, bad or non-optimal exposure, and vibrations that can result in blurred images. While these three example conditions are discussed in reference to FIGS. 10-16, it will be understood that there can be other conditions that can adversely affect the quality of images.

Figure 10:
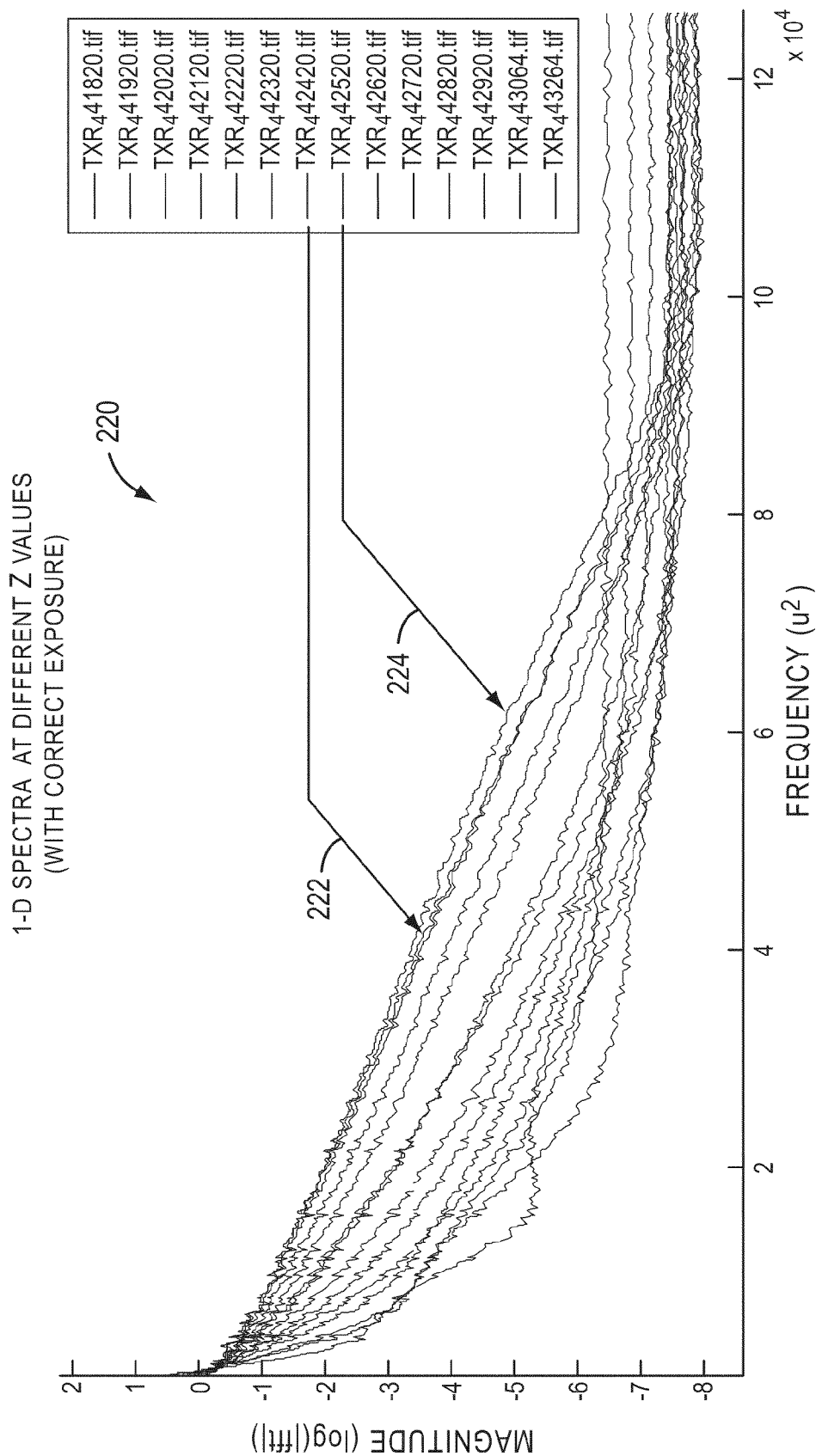
FIG. 10 shows various examples of one-dimensional frequency space representation curves for different focus settings, showing that in-focus settings may yield greater measures of linearity than those of unfocused settings.

FIG. 10 shows a plurality of one-dimensional spectra 220 obtained from isocentric-average representations of fast Fourier transforms of corresponding measured intensity distributions. The spectra 220, plotted as log(|fft|) versus u2, correspond to different z values of focus. All of the example spectra 220 have been obtained at correct exposures.

Figure 11:
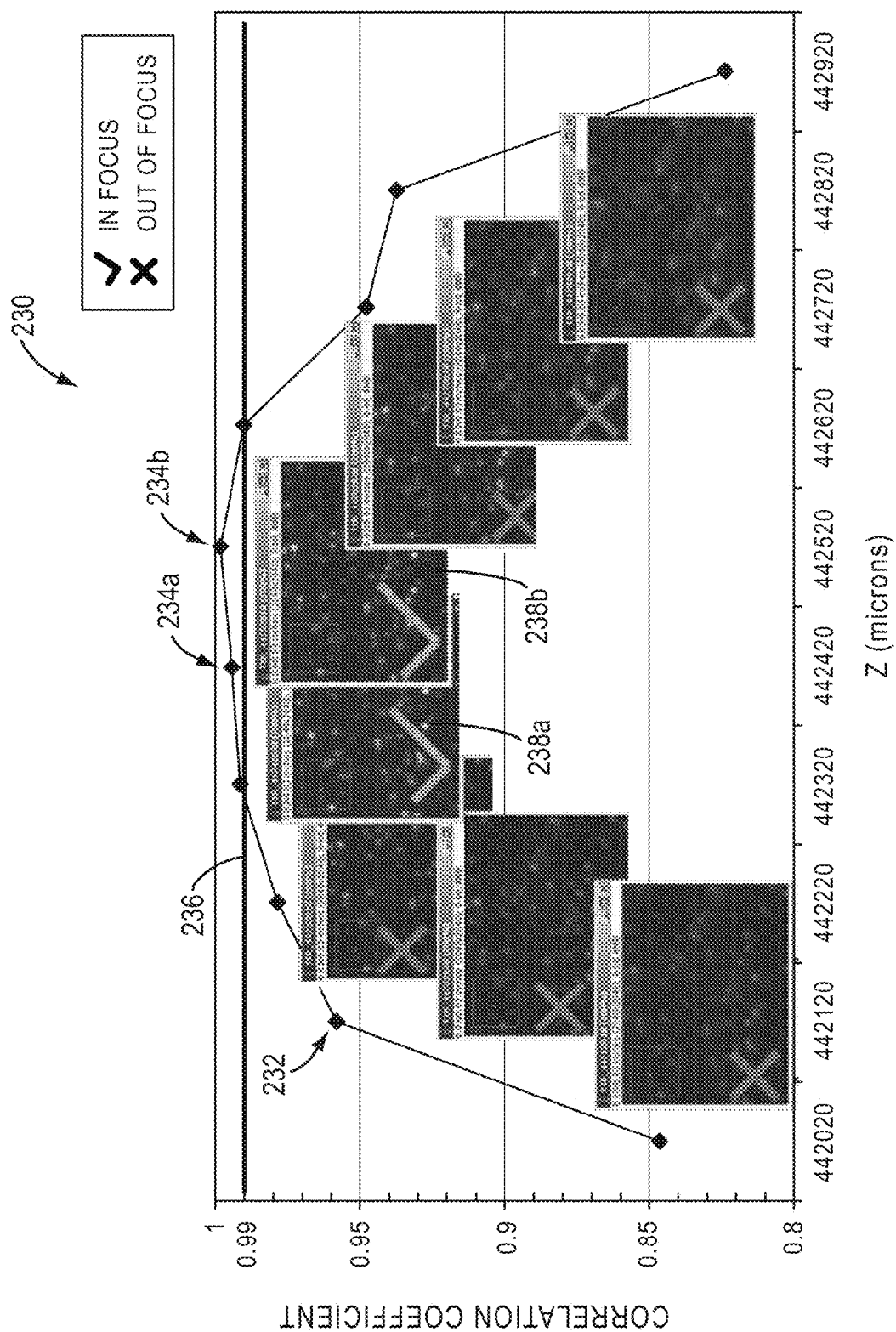
FIG. 11 shows that in certain embodiments, a correlation coefficient of linearity can provide the measure of linearity of FIG. 10, and therefore allow determination of a focus quality of the image.

FIG. 11 shows a plot 230 of correlation coefficient values 232 obtained from linear fitting of the spectra 220 at different z values. As shown, data points 234a and 234b have correlation coefficients greater than a threshold 236 selected to be at approximately 0.99. As shown in the accompanying photographs 238a and 238b, various beads or features in the images are relatively sharp and in focus when compared to other images whose correlation coefficients are less than the threshold.

As shown in FIG. 10, the example in-focus data points 234a and 234b (FIG. 11) correspond to spectra indicated by arrows 222 and 224, respectively. One can see that the in-focus spectra 222 and 224 have greater linear portions, as well as linearity of such portions.

It will be understood that the threshold 236 value of 0.99 is simply an example. Other values can be selected. For example, lowering the threshold to a value of 0.98 will have an effect of designating the two data points corresponding to z values "442320" and "442620" as being in-focus. Threshold determination may be defined as a preset value or range of values dynamically determined or set by other desired methods. As such threshold determination is not considered to be limited solely to those methods described and may be adapted as desired.

Figure 12:
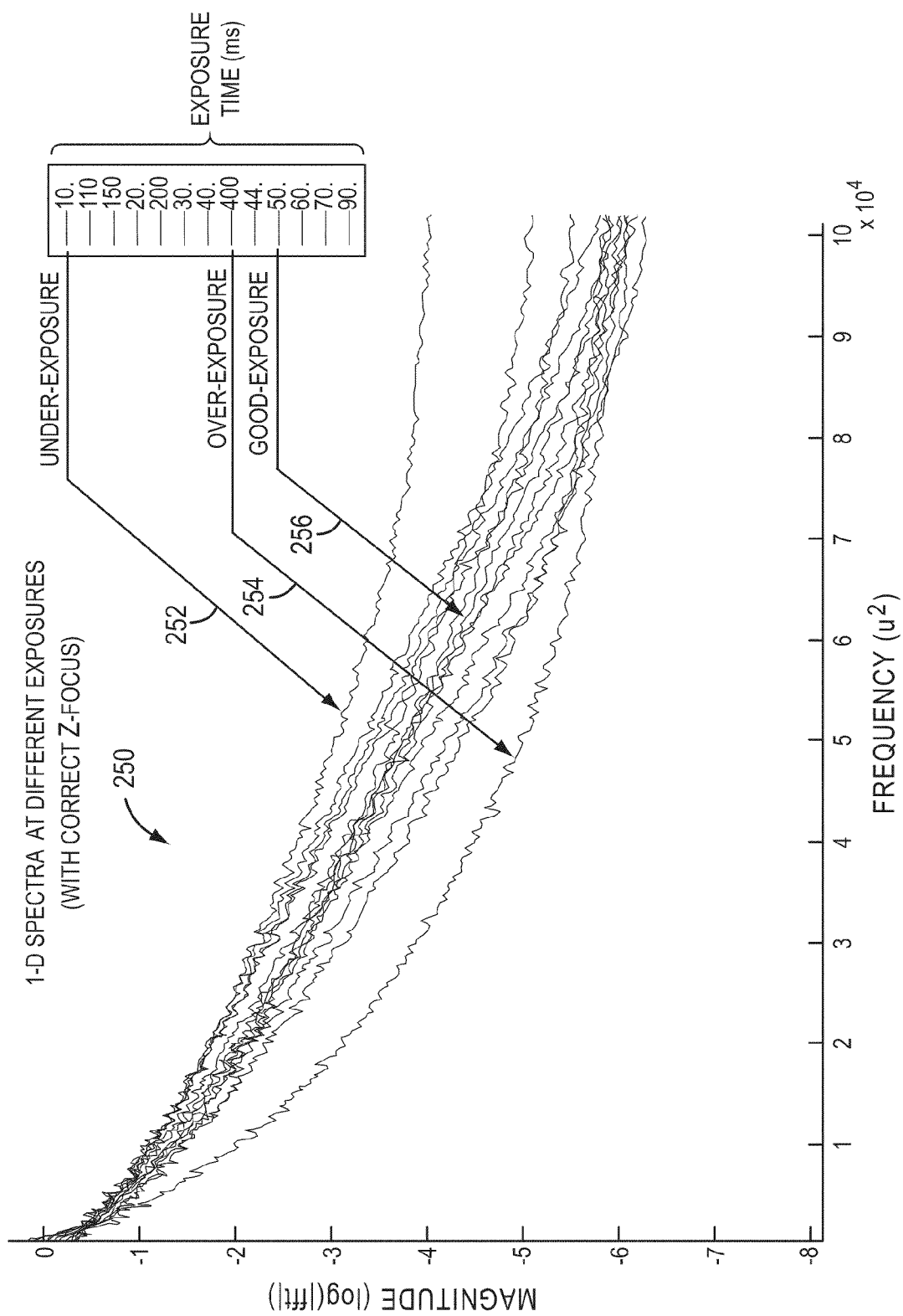
FIG. 12 shows various examples of one-dimensional frequency space representation curves for different exposure settings, showing that properly exposed images yield greater measure of linearity than those of over- or under-exposed images.
Figure 13A:
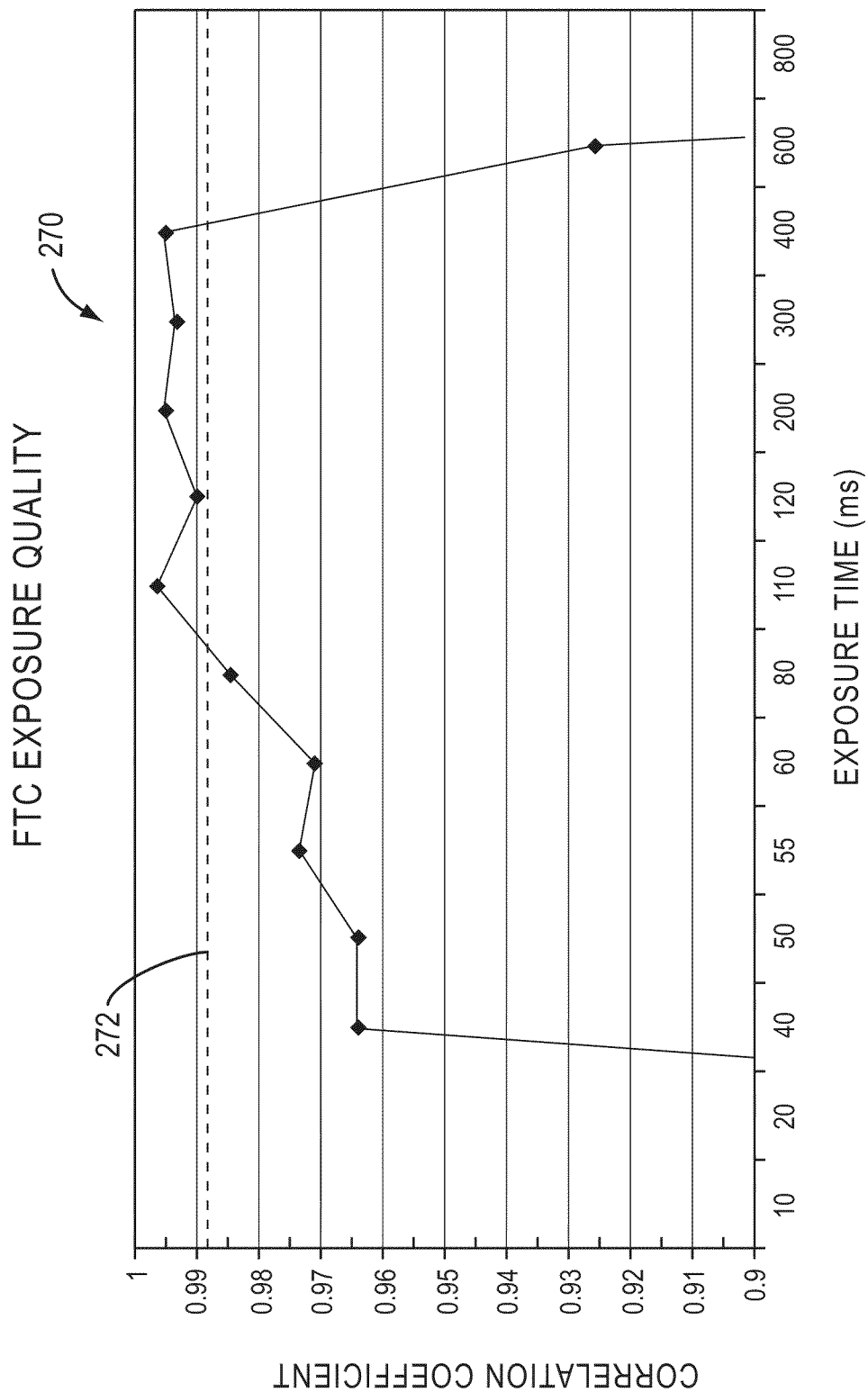
FIGS. 13A-13D show that in certain embodiments, a correlation coefficient of linearity can provide the measure of linearity of FIG. 12, and therefore allow determination of an exposure quality of the image.
Figure 13B:
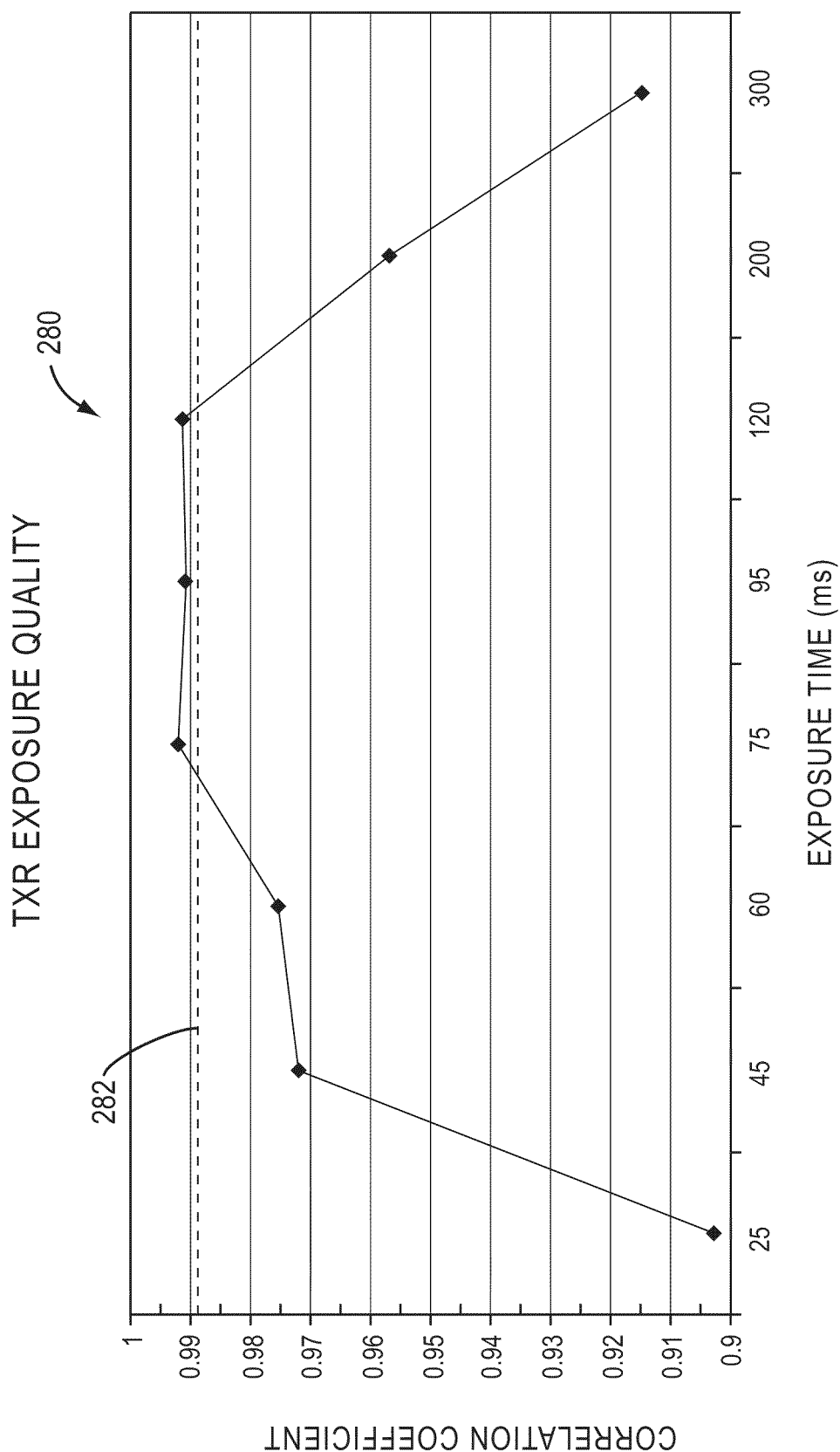
Figure 13C:
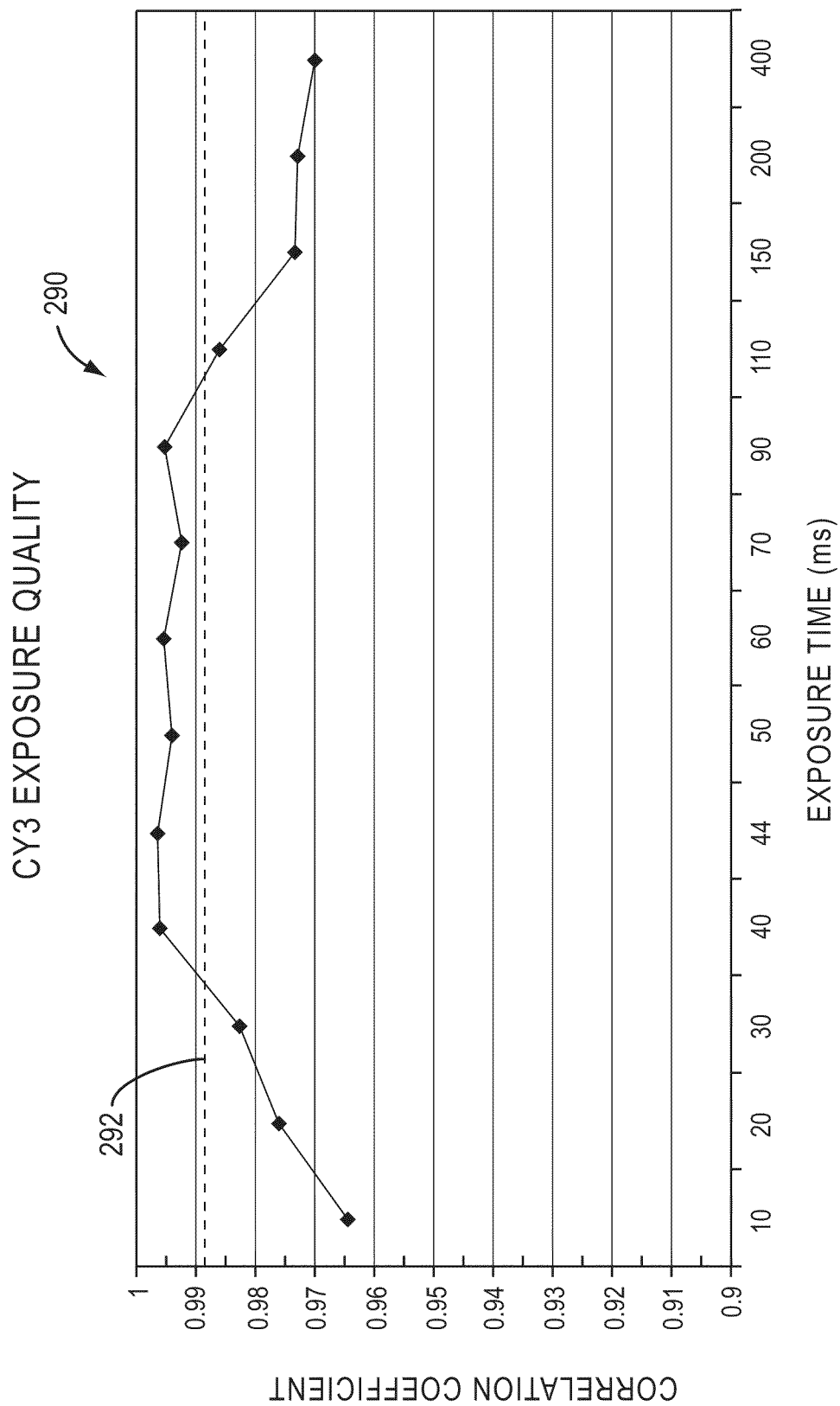
Figure 13D:
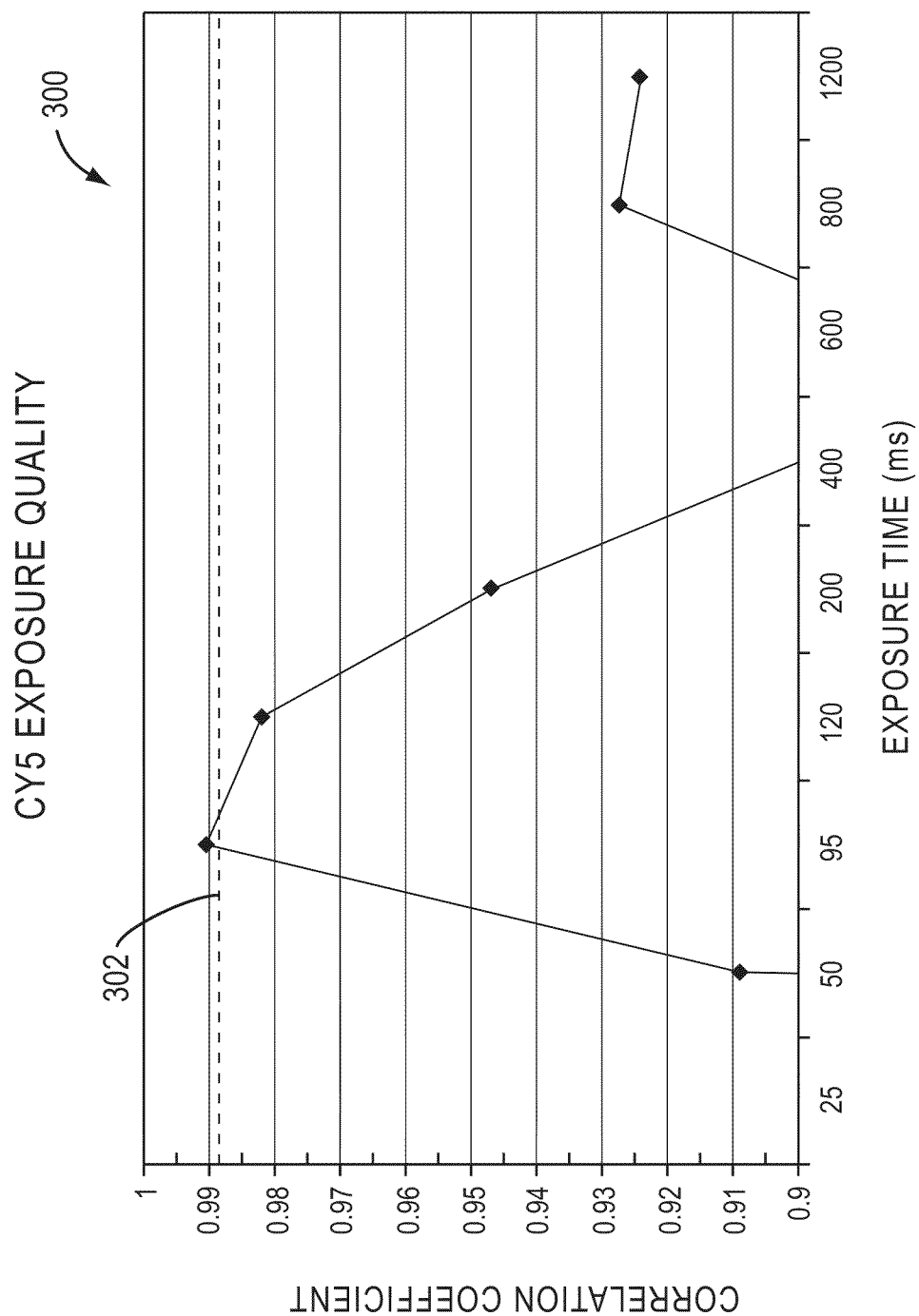

As stated herein, exposure is another example condition that can affect the quality of an image. FIG. 12 shows a plurality of one-dimensional spectra 250 obtained from iso-centric-average representations of fast Fourier transforms of corresponding measured intensity distributions. The spectra 250, plotted as log(|fft|) versus u2, correspond to different exposure settings. All of the example spectra 250 have been obtained with correct focus.

FIGS. 13A-13D show plots (270, 280, 290, 300) of correlation coefficient values obtained from linear fitting of the spectra at different exposure settings, similar to the example shown in FIG. 12. The example plot 270 corresponds to a configuration where a selected fluorescent dye (FTC) is used; the example plot 280 corresponds to a configuration where another selected fluorescent dye (TXR) is used; the example plot 290 corresponds to a configuration where a further fluorescent dye (CY3) is used; and the example plot 300 corresponds to a configuration where CY5 fluorescent dye is used.

As shown in FIG. 12, spectra whose exposure are considered to be good (indicated by arrows 256) have generally greater linear portions, as well as linearity of such portions, than those considered to be under-exposed (indicated by an arrow 252) and over-exposed (indicated by an arrow 254).

As shown in FIGS. 13A-13D, an example threshold value (272, 282, 292, 302) is selected at approximately 0.99. Data points that exceed the threshold can be considered to have correct exposures. As with the focus-based examples of FIGS. 10 and 11, the threshold values can be adjusted to different values. For example, the threshold 302 of FIG. 13D can be lowered to be more inclusive to avoid situations where all or most of exposures are deemed bad.

Figure 14:
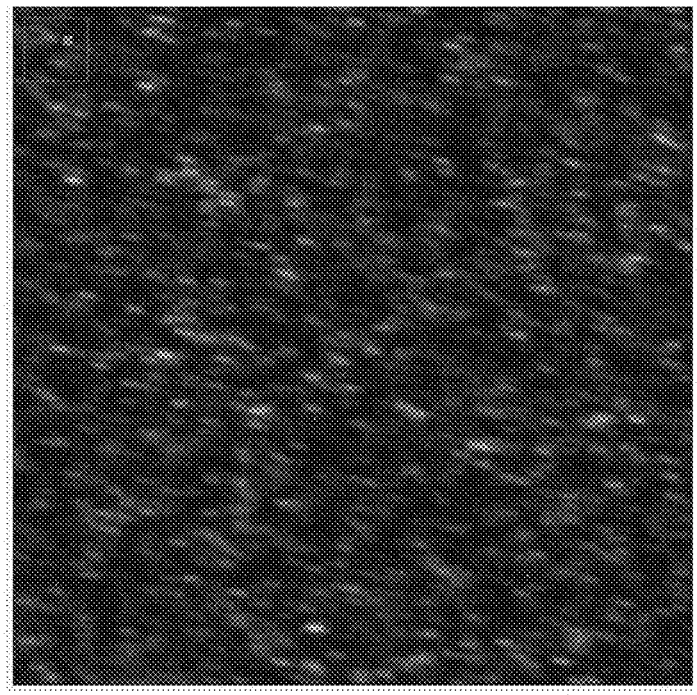
FIGS. 14 and 15 show example images of blurred sequencing beads or particles due to vibration, where such a condition can be detected by an assessment similar to that of FIGS. 10-13.

As stated above, vibration is another example condition that can affect the quality of an image. FIG. 14 shows an example blurred image 310 resulting from vibrations. As shown, various images of the beads are elongated rather than being symmetrical.

Figure 15:
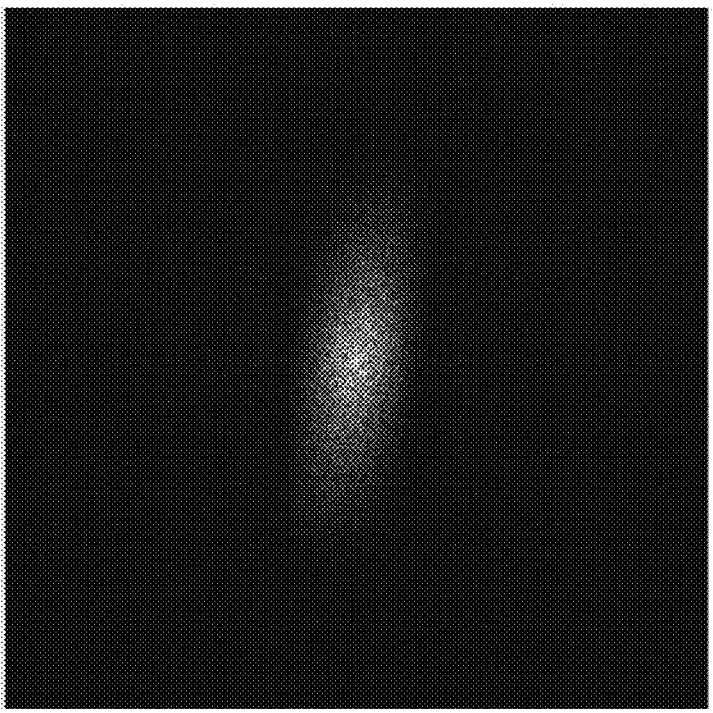

FIG. 15 shows an enlarged view of a bead or feature 320 whose image is elongated, for example due to vibration along the elongation direction. As described in reference to FIG. 7B, an asymmetric intensity distribution can result in a one-dimensional isocentric-average spectrum deviating from a symmetric or substantially symmetric distribution such as that of FIG. 7A or a bead or feature image not subjected to vibrations.

In certain embodiments, a condition resulting from vibration can be detected by fitting an ellipse to a two-dimensional FFT distribution of a bead or feature image. Such fitting can be triggered, for example, when the bead or feature image quality is determined to be bad or non-optimal. From the elliptical fit, a major axis can be determined for the bead or feature image. Such major axes can be determined for similar bead or feature images.

In the example image shown in FIG. 14, the beads' elongation directions (major axes) are generally aligned in one direction, thus indicating that the vibration is along that direction. If the vibration is generally along the stage movement direction, then the vibration is likely due to the stage not having settled fully. In such a situation, a correction can include an increase in the delay time after the completion of stage movement. If the major axes are aligned in a substantially random manner, then the vibration is likely due to some other systematic effect. Based on such diagnosis, appropriate corrective actions can be effectuated. An example of implementing such corrections is described herein in greater detail.

Figure 16:
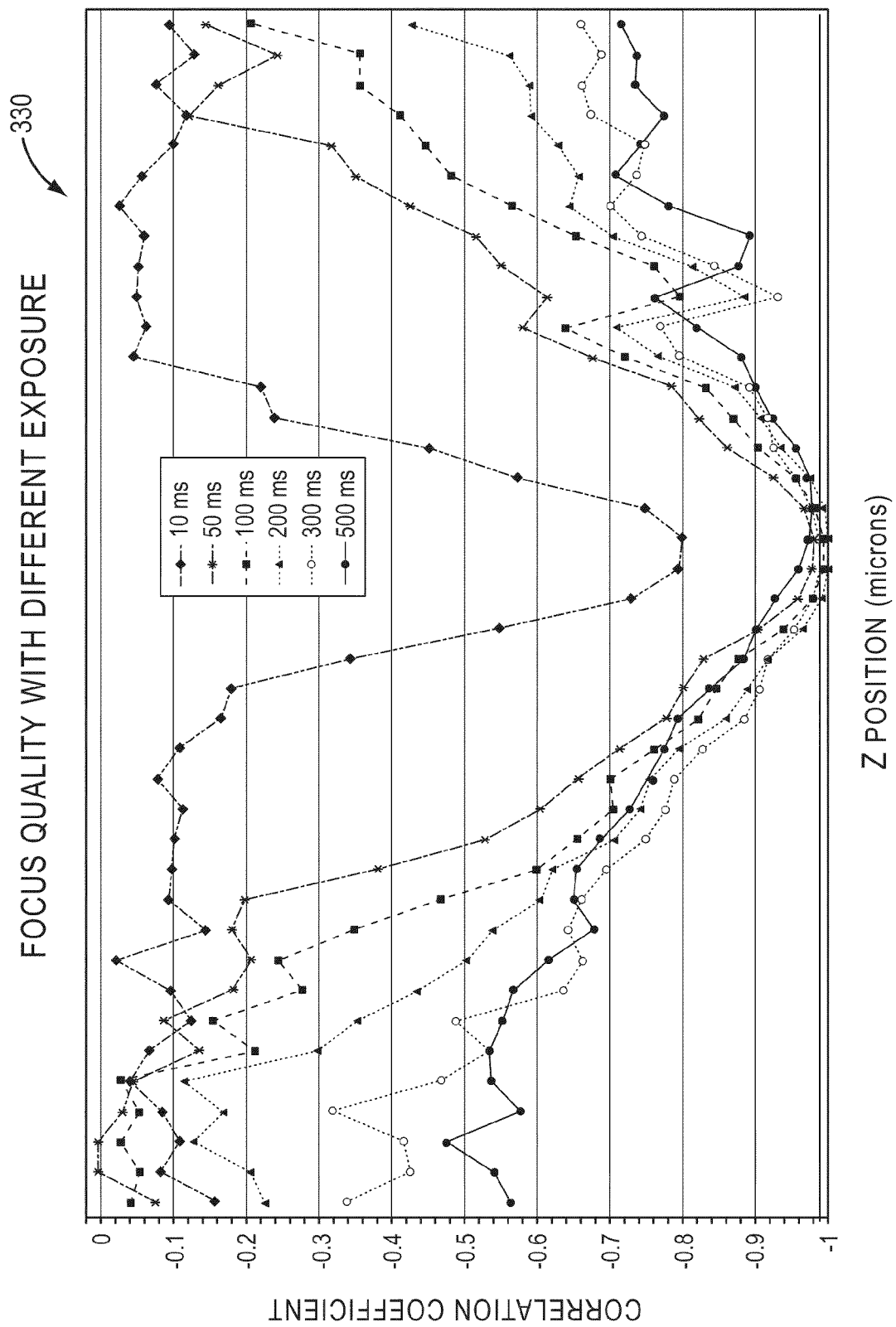
FIG. 16 shows an example of how focus quality can be affected by different exposures.

In certain situations where an image quality is found to be poor, it may not be readily apparent as to what condition(s) contributed to the poor image quality. By way of example, FIG. 16 shows a plurality of focus quality plots 330 obtained at different exposure conditions. Again, an example threshold 332 is shown to be selected at about –0.99.

Based on the example plots, exposure times of 100 ms (filled square) and 200 ms (filled triangle) appear to be appropriate exposure conditions so as to allow selected focus quality values that exceed the threshold 332. A longer exposure of 300 ms (unfilled circle) appears to allow selected focus quality values to be at or about the threshold 332, but not as good as the 100 ms and 200 ms cases. An even longer exposure of 500 ms (filled circle) does not appear to allow any focus quality values to exceed the threshold 332.

Likewise, a shorter exposure of 50 ms ("X") also does not appear to allow any focus quality values to exceed the threshold 332. An even shorter exposure of 10 ms (filled diamond) results in even its best focus quality values being relatively far from the threshold 332.

Thus, in certain embodiments, an image quality value can be obtained and assessed, regardless of knowing what contributed to the value. Such an assessment can facilitate quick and efficient image assessments during, for example, a scan of multiple images from a given slide or substrate to evaluate the focus or quality of the imaging process.

As described herein, certain slide-imaging situations involve scanning of a slide at various X-Y positions on the slide. In certain embodiments, it may be preferable to perform a satisfactory imaging or appropriate disposition before making a relatively large movement of the slide. For example, it may be preferable to move the slide or substrate to a nearby position upon completion of camera or CCD exposure; and if that image from the just-completed exposure is determined to be bad, the slide or substrate can be moved back relatively quickly to re-acquire the image. This example configuration may be preferable if, for example, the stage movement time is relatively small.

Thus, in certain embodiments, image assessment and correction can be performed prior to moving the slide to an X-Y position that is relatively far from the image location on the slide or substrate. In certain embodiments, image assessment and determination for correction can be performed while the next image is being acquired and before the stage moves on to acquire the following image. The correction, if needed, can be achieved by having the stage move the slide back to the position where image re-acquisition is to occur.

In certain embodiments, an image quality management can be depicted as a process 340. In a process block 342, an image can be obtained. In a process block 344, the image can be processed. In certain embodiments, such processing can include determination of one or more image quality values similar to that described above in reference to FIGS. 10-16. In a decision block 346, the process 340 can determine whether the image is bad. If the answer is "No," the image can be kept in a process block 350. If the answer is "Yes," a corrective action can be taken in a process block 348.

Figure 17:
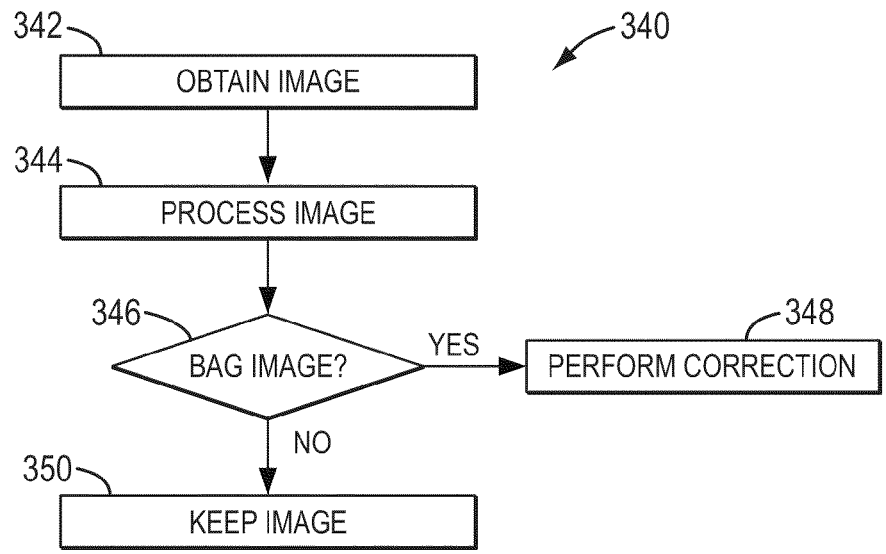
FIG. 17 shows that in certain embodiments, a bad image due to, for example, bad focus, bad exposure, and/or vibration, can be detected so as to allow correction of such condition(s)
Figure 18:
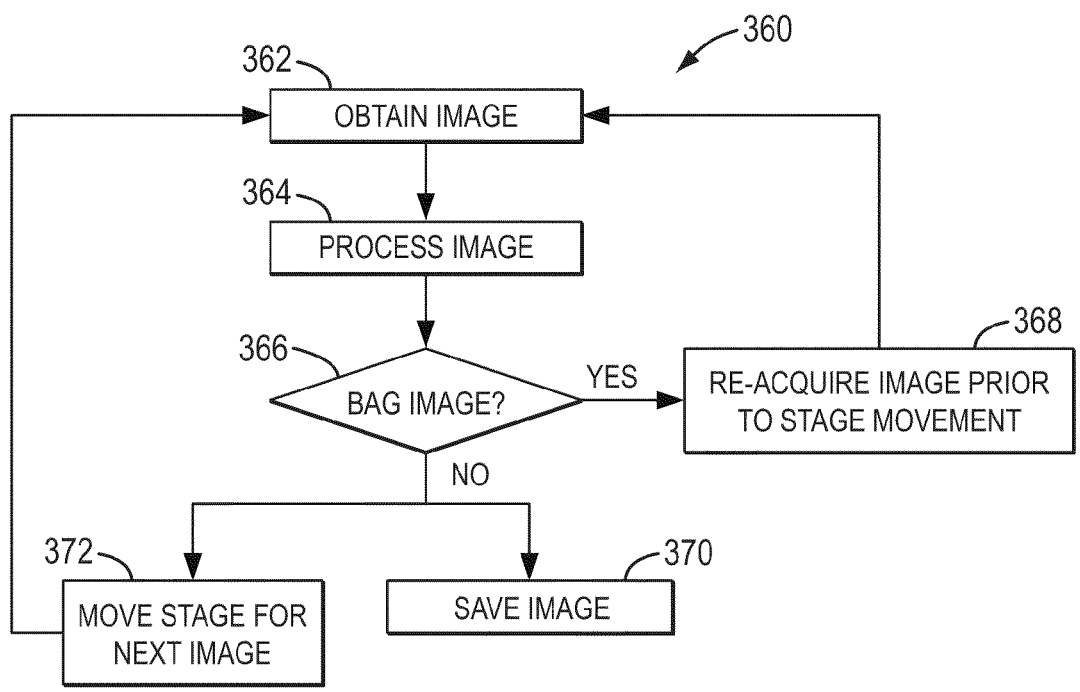
FIG. 18 shows that in certain embodiments, bad-image determination and correction of the image can be performed in a substantially real-time manner.

FIG. 18 shows one embodiment of a process 360 that can further implement a feedback system to the process 340 of FIG. 17. In a process block 362, an image can be obtained. In a process block 364, the image can be processed. In certain embodiments, such processing can include determination of one or more image quality values similar to that described in reference to FIGS. 10-16. In a decision block 366, the process 360 can determine whether the image is bad. If the answer is "No," the image can be saved in a process block 370, and the stage can be moved for next image in a process block 372. If the answer is "Yes," the process 360 can re-acquire the image in a process block 368.

FIG. 18 shows an example of how image assessment can be implemented into a scanning process so as to allow more efficient correction of one or more conditions as the scanning progresses. In certain embodiments, there are other types of corrections that can be implemented in response to the image assessment.

Figure 19:
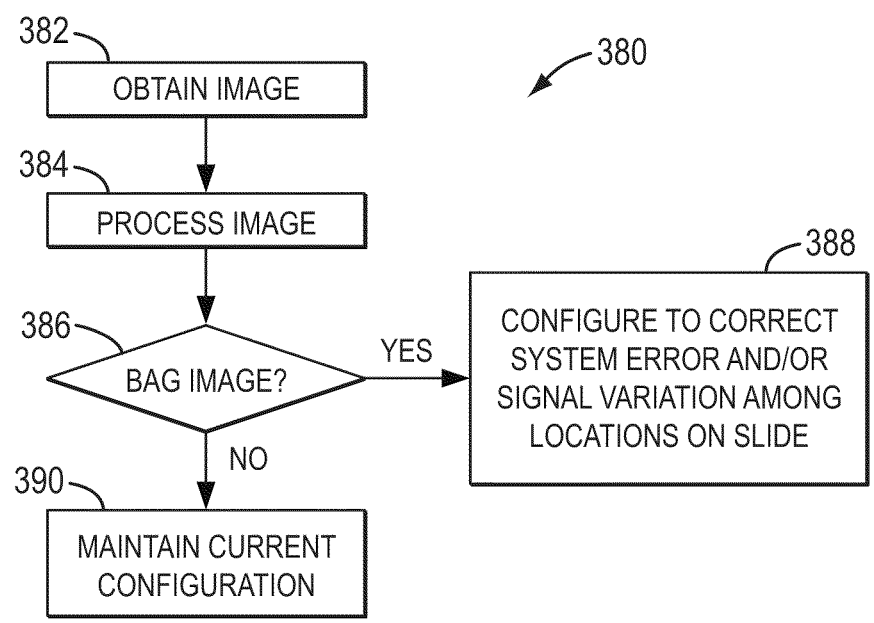
FIG. 19 shows that in certain embodiments, bad-image determination can be utilized to detect and correct system errors and/or other conditions such as signal variations on a slide.

FIG. 19 shows an example of a process 380 where the correction in response to the image assessment can be a type other than corrections performed during the scan on an image-by-image basis. In a process block 382, one or more images can be obtained. In a process block 384, the obtained image can be processed. In certain embodiments, such processing can include determination of one or more image quality values similar to that described in reference to FIGS. 10-16. In a decision block 386, the process 380 can determine whether the image is bad. If the answer is "No," the process 380 can maintain the current operating configuration in a process block 390. If the answer is "Yes," the process 380 can, in a process block 388, perform a configuration to correct, for example, system error and/or effects such as signal variations that may exist among different locations of the slide. Examples of such corrections are described below in greater detail.

Figure 20:
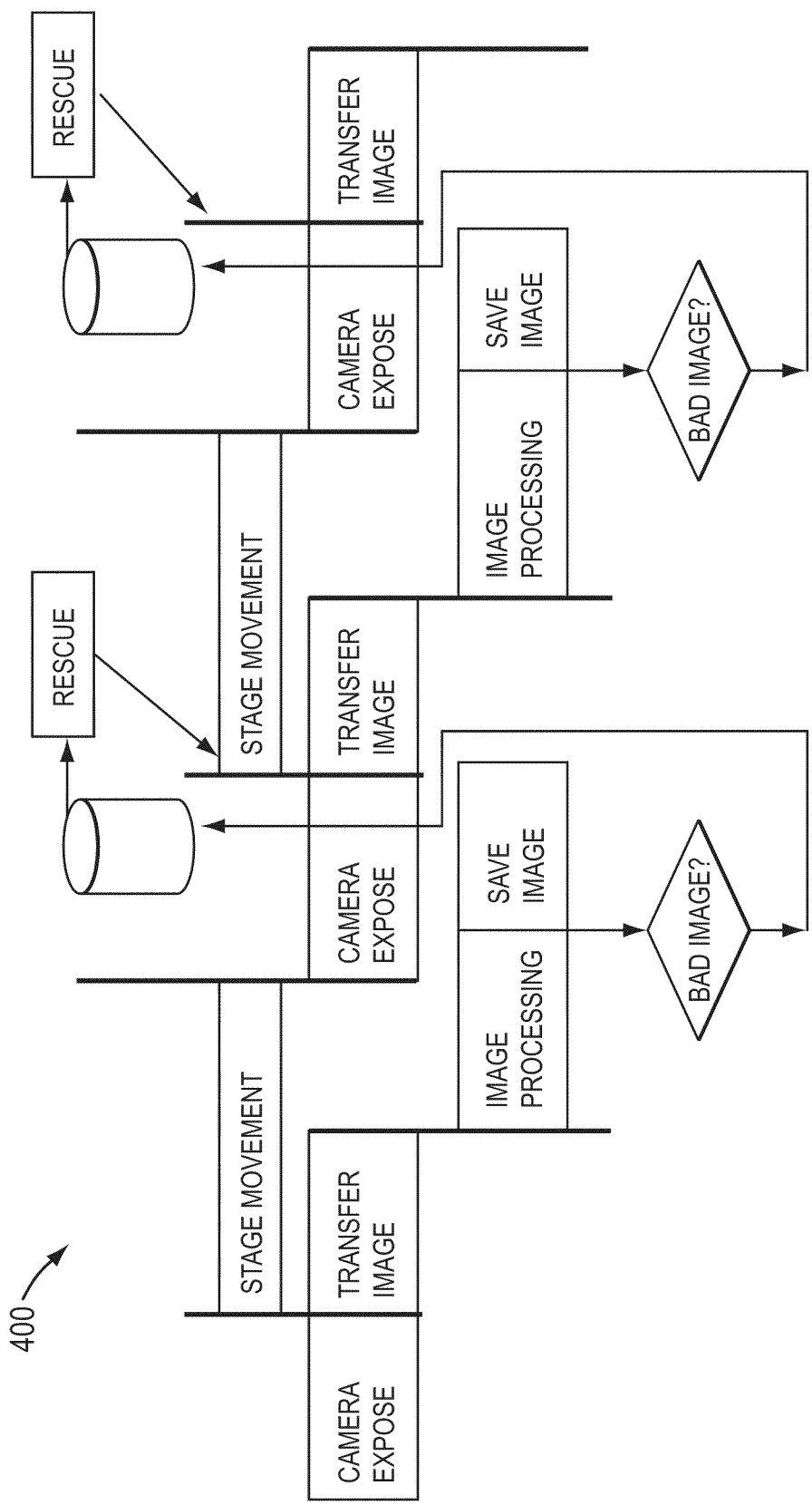
FIG. 20 shows an example schematic diagram of a substantially real-time image assessment and correction process in a sequence of image acquisitions.
Figure 21A:
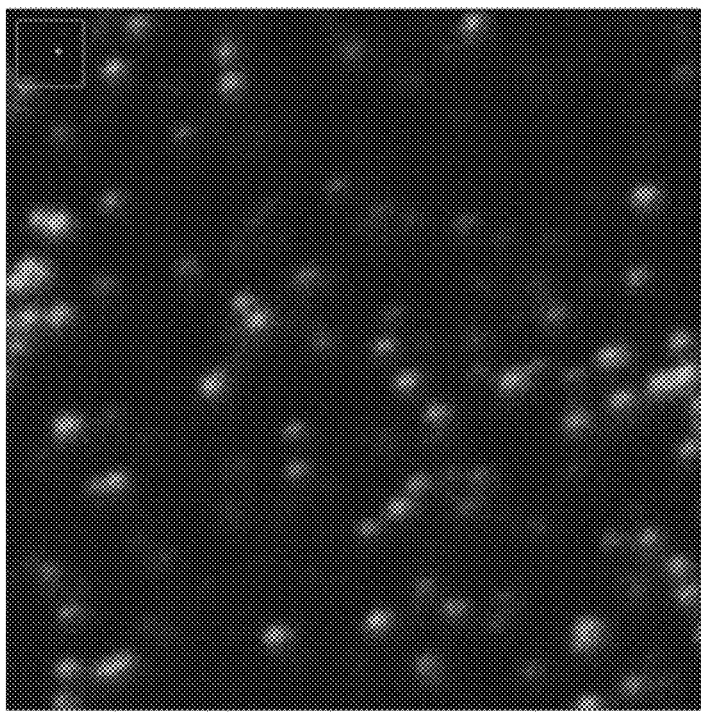
FIGS. 21A and 21B show, by way of example, an uncorrected image and a focus-corrected image.
Figure 21B:
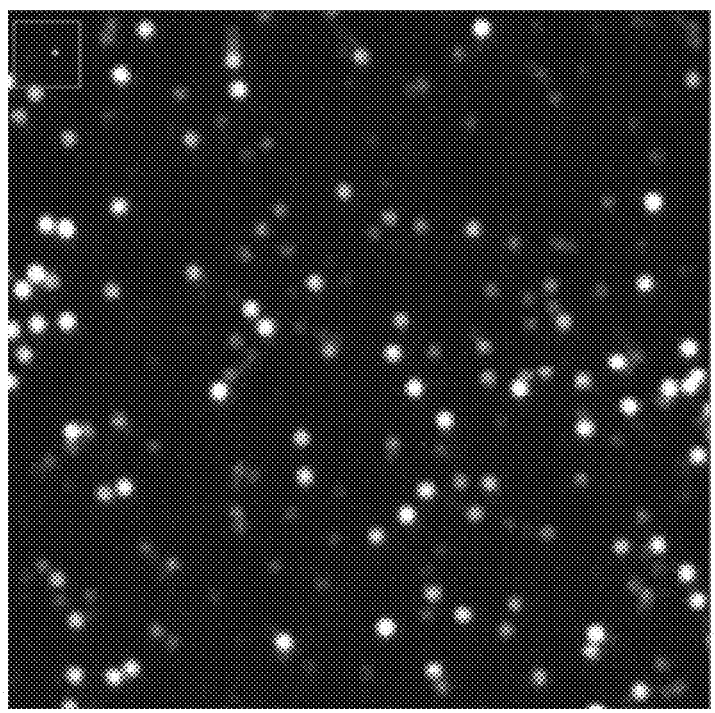

FIG. 20 shows a schematic diagram of an example sequence 400 of image acquisitions during a scanning or imaging process. As shown, the example sequence can include image assessment and correction processes as described in reference to FIG. 18.

As shown at the left end of a sample of the sequence 400, camera exposure can be followed by stage movement and transfer of image. The stage movement can be made to the next imaging position with an assumption that the image just obtained will be a good image. As shown in the sequence 400, the stage movement can be followed by camera exposure of the next image.

As also shown in the sequence 400, the transfer of the just-obtained image can occur while the stage movement is in progress. The transfer of image can be followed by processing of the image. In certain embodiments, such image processing can be performed in a multithreading manner, facilitated by buffers, along with other tasks such as camera control task, to decrease the overall scanning time and increase the throughput of the scanning process.

As shown in the sequence 400, the image processing (including, for example, image assessment) can be followed by either saving of the image (if determined to be a good image) or determination that the image is bad or non-optimal. Upon determination that the image is bad or non-optimal, a corrective action can be triggered, as indicated by the "Rescue" block. In certain embodiments, upon the trigger of the Rescue mode, the corrective action can be executed prior to the next scheduled stage movement to allow movement to (if needed) re-acquire the image that has been found to be bad or non-optimal.

Based on the example scanning sequence of FIG. 20, one can see that assessment and correction of bad images can be performed in real-time. For the purpose of description, the term "real-time" will be understood as having ordinary and customary meaning, including but not limited to an interpretation where a computing application processes information and responds as generally rapidly as necessitated by the process being controlled. In the example sequence 400 of FIG. 200, image processing and determination to trigger Rescue can be in real-time, since such processing and response can be performed prior to the next stage control.

Effectiveness of some or all of the features described herein can be shown by way of examples in FIGS. 21-25. In FIGS. 21A and 21B, a qualitative comparison is depicted between an out-of-focus (determined to be bad in the assessment) 420 and a re-acquired image 430 with corrected focus. As shown, the improvement in the image quality is significant.

Figure 22A:
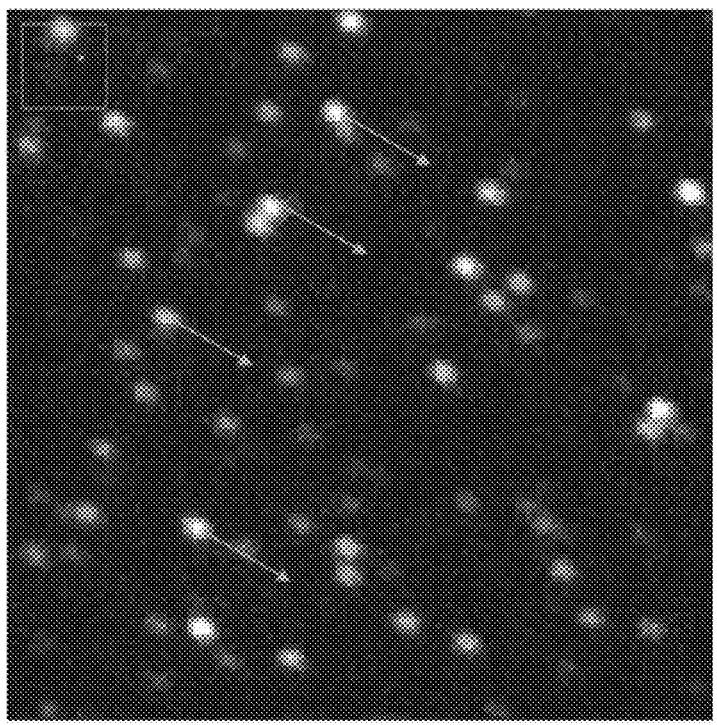
FIGS. 22A and 22B show by way of example, an uncorrected image and a corrected image with reduced vibrations.
Figure 22B:
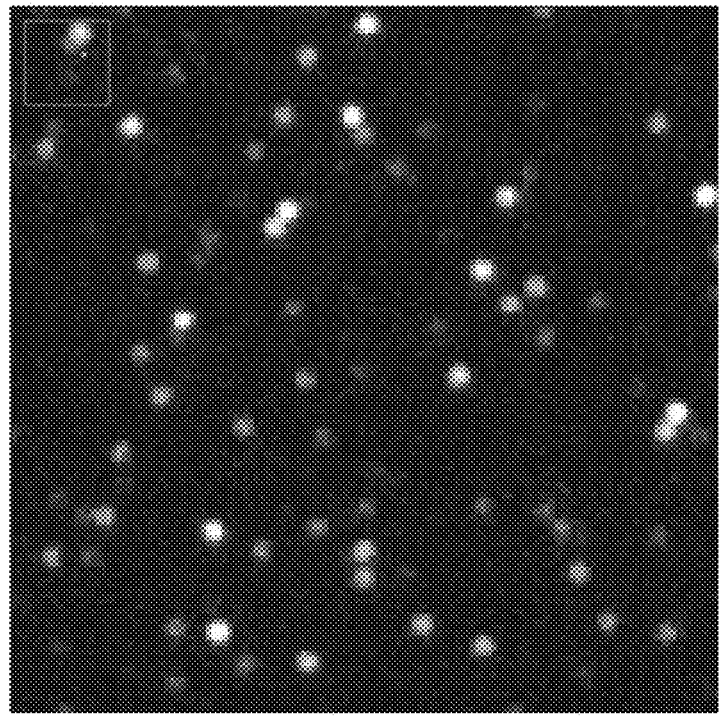

In FIGS. 22A and 22B, a qualitative comparison is depicted between a jittery image (determined to be bad in the assessment) 440 and a re-acquired image 450 with reduced vibrations. Again, the improvement in the image quality is significant.

Figure 23:
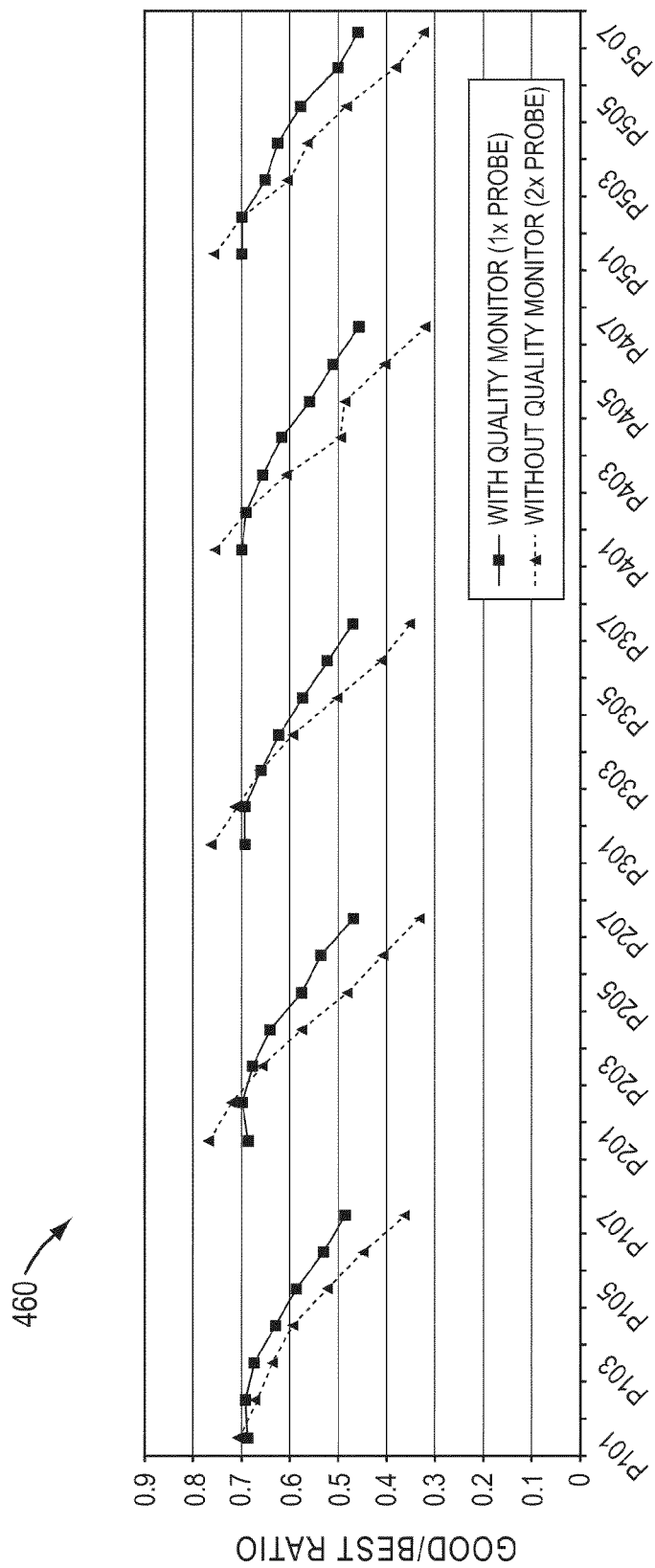
FIG. 23 shows that in certain embodiments, monitoring of image quality and corrections, if needed, can maintain a greater amount of usable images during a scanning process.

In FIG. 23, a quantitative comparison 460 shows how image quality assessment and rescue can improve the overall performance of imaging of the sequencing beads or features associated with a biological sample analysis method. In certain embodiments when sequencing nucleic acid templates through a plurality of cycles, or iterations it may be observed that image quality can degrade at higher cycle numbers or iterations. For example each cycle can involve cleaving of portions of probe, primer or template fragments (e.g., photo-cleaving via UV light), and such cleaving processes can result in a decrease in probe, primer, or template concentration. Such decrease in concentration can reduce a given bead or features image's signal-to-noise ratio, and thus the observed degradation in image quality.

It is also observed that a decrease in probe density can degrade the quality of individual bead or feature images. Generally, higher concentrations of labeled probe result in more such probes being present and available for attaching to the templates; thus, the resulting bead or feature image will likely have greater signal-to-noise ratio.

As shown in FIG. 23, the triangular and square data points represent respective fractions of good beads or features for a given panel. For the purpose of description, a bead, feature, or area of imaging interest can be considered to be good if its signal-to-noise ratio is greater than some threshold value. For example, each bead or feature can have signals coming from different channels (e.g., fluorescent signals from dyes including, FAM, TXR, CY5 and CY3), and the signal-to-ratio can be defined as a ratio between the four channels' second maximum brightness value and the maximum brightness value.

Data points P101 to P107 represent a given panel's fraction of good beads during seven cycles of ligations using primer 1. Data points P201 to P207 represent the same using primer 2, and so on.

As shown, the triangle data points represent a configuration of scanning ligation cycles with a given concentration of labeled probes, where image quality is not monitored by assessment. As the cycle number increases, there is certain decrease in each panel's performance for reasons previously described.

As also shown, the square data points represent a configuration of scanning cycles with a concentration of labeled probes that is about half of the unmonitored case (triangle data points), where image quality is monitored by assessment (and rescue if needed). As the cycle number increases, there is a decrease in each panel's performance, again, for reasons previously described. However, the decrease in performance is at a significantly slower rate than that of the unmonitored case, even though the monitored configuration is already at a disadvantage due to its lower probe concentration.

It is also noted in FIG. 23 that the first cycle for each primer case yields results where the image quality of unmonitored case (triangle) is generally better than that of the monitored case (square). This can be due to the previously described effect where higher concentration of labeled probes generally results in greater signal-to-noise ratio in the image. As shown, despite the inherent disadvantage of lower probe concentration in the monitored case, performance of the monitored case is generally better, especially as the cycle number increases where signal-to-noise ratio decreases. Such a feature can be useful since the monitoring process can improve performance better than simple doubling of the probe concentration. Moreover, such a feature can be particularly advantageous when the cost of supplying the probes per run is relatively high.

Figure 24A:
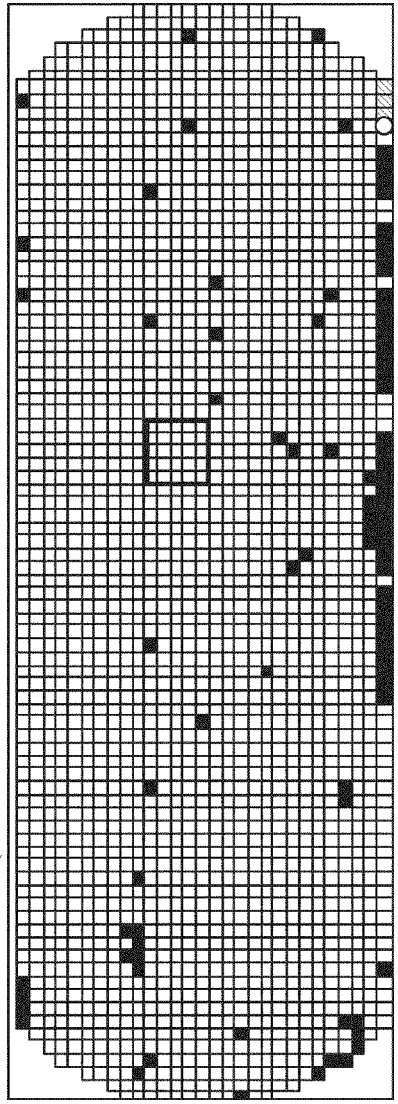
FIG. 24A shows a plan view of an example slide with a plurality of panels populated with sequencing beads or particles, with the dark shaded panels indicating a rescued status where image assessments and corrections resulted in such panels becoming useful.

The enhanced panel performance via image quality monitoring can be attributed the ability to rescue images that would otherwise be discarded if not assessed for image quality. An example of panels being rescued and thereby providing an enhanced slide performance is shown in FIG. 24A, where an example slide 470 is shown to have an array of panels. In the depiction of the example slide 470, the darkened panels represent panels that have been rescued via the image quality monitoring process.

Figure 24B:
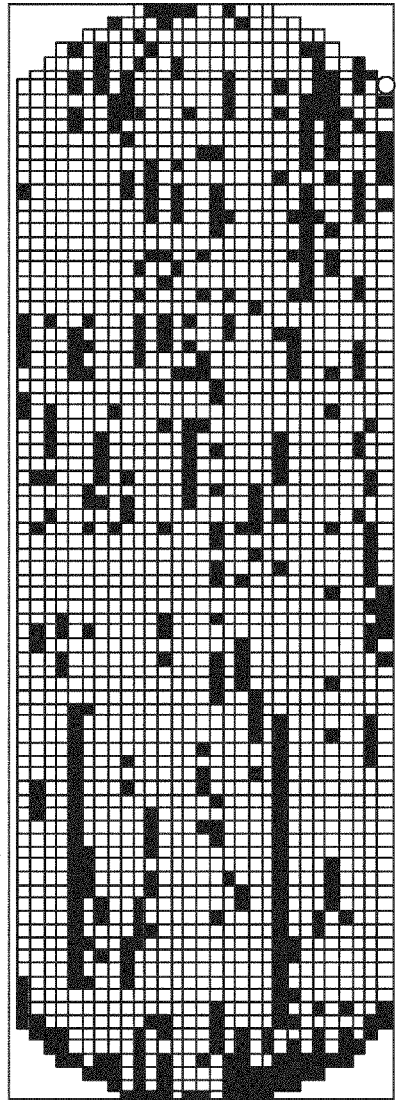
FIG. 24B shows a similar example slide with even greater number of dark shaded panels again indicating rescued status, where the slide was subjected to motion due to thermal fluctuations.

In FIG. 24B, where another example slide 480 is shown, the number of rescued panels is drastically larger than that of the slide 470. The difference between the example slides 470 and 480 is that slide 470 is not subjected to thermal fluctuation, whereas slide 480 is.

Figure 25:
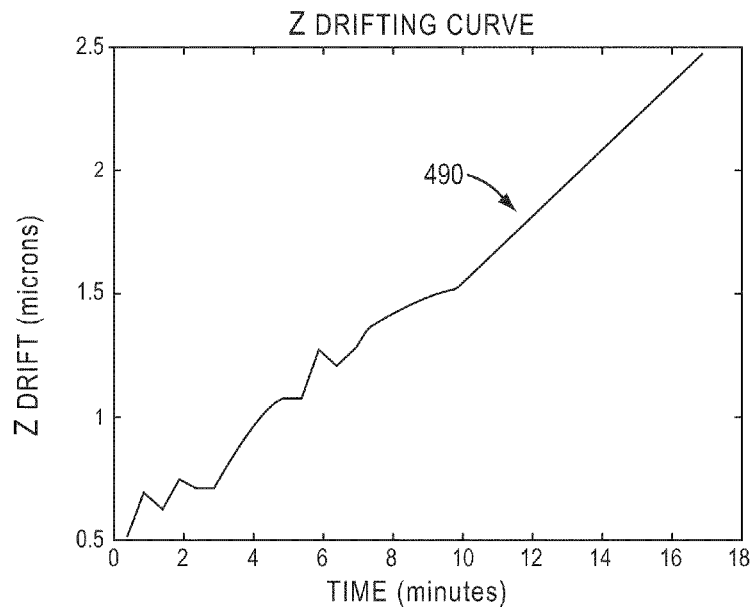
FIG. 25 shows by way of example that in certain situations, thermal fluctuation can occur via thermal cross-talk between different flow cells or reaction areas.

An example effect of thermal fluctuation is shown in FIG. 25, where Z-drift of the stage is plotted (curve 490) as a function of time subjected to an induced thermal fluctuation. While the example result of the thermal fluctuation is induced in FIG. 25, there are a variety of situations where thermal fluctuations can occur. By way of a non-limiting example, in certain embodiments, an analysis system can have two or more flow cells or sample chambers; and such flow cells or sample chambers can be subjected to thermal cross-talk. For example, if one flow cell's temperature is adjusted, another flow cell's temperature can be undesirably affected.

As shown in FIG. 25, the focus of a slide, substrate, or surface can drift significantly while the stage is subjected to thermal fluctuation. Consequently, panels that are subject to such Z-drifts while imaging can be discarded as bad panels if not monitored for quality. With image quality monitoring, however, relatively large number of such thought-to-be bad or non-optimal panels can be rescued so as to provide an enhanced slide performance.

Figure 26:
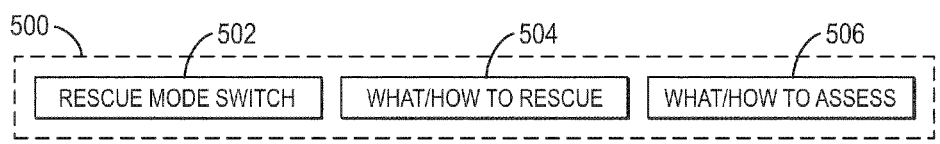
FIG. 26 shows that in certain embodiments, a scanning system can include a rescue mode switching component, a component that facilitates what and/or how to perform the rescue, and/or a component that facilitates what and/or how to perform the assessment.

In certain embodiments, the foregoing non-limiting examples of enhancement in scanning performance can be achieved and/or facilitated by a monitoring component 500 as shown in FIG. 26. The monitoring component 500 can include a component 502 whose functionality can include a switch that determines whether a panel or a group of panels should be rescued. An example of such functionality is described below in greater detail.

The monitoring component 500 can also include a component 504 that can determine what to rescue and/or how to perform such rescue. An example of such functionality is described below in greater detail.

The monitoring component 500 can also include a component 506 that can determine what to assess and/or how to perform such assessment. An example of such functionality is described below in greater detail.

Figure 27:
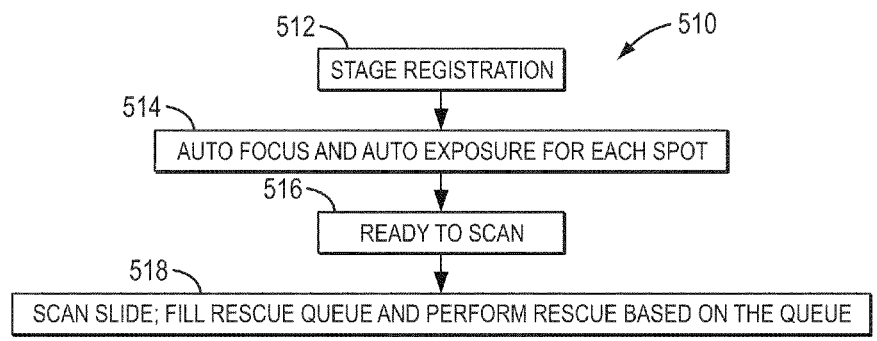
FIG. 27 shows an example process for scanning a slide or substrate.

In FIG. 27, an example process 510 shows how rescue operations can be implemented in a slide or substrate scanning situation. In a process block 512, stage registration can be performed to, for example, define how slide movements are to be carried out. In a process block 514, auto focus and auto exposure can be obtained for groups of panels (referred to as "spots" in FIG. 27). For a given spot, such focus and exposure settings can be the default settings for panels in that spot. In a process block 516, the process 510 can be ready to scan. In a process block 518, the process can scan the slide and perform rescue operations as needed. In certain embodiments, such rescue operations can be implemented via filling of a rescue queue and executing rescues based on such a queue. An example of such rescue queue is described below in greater detail.

Figure 28:
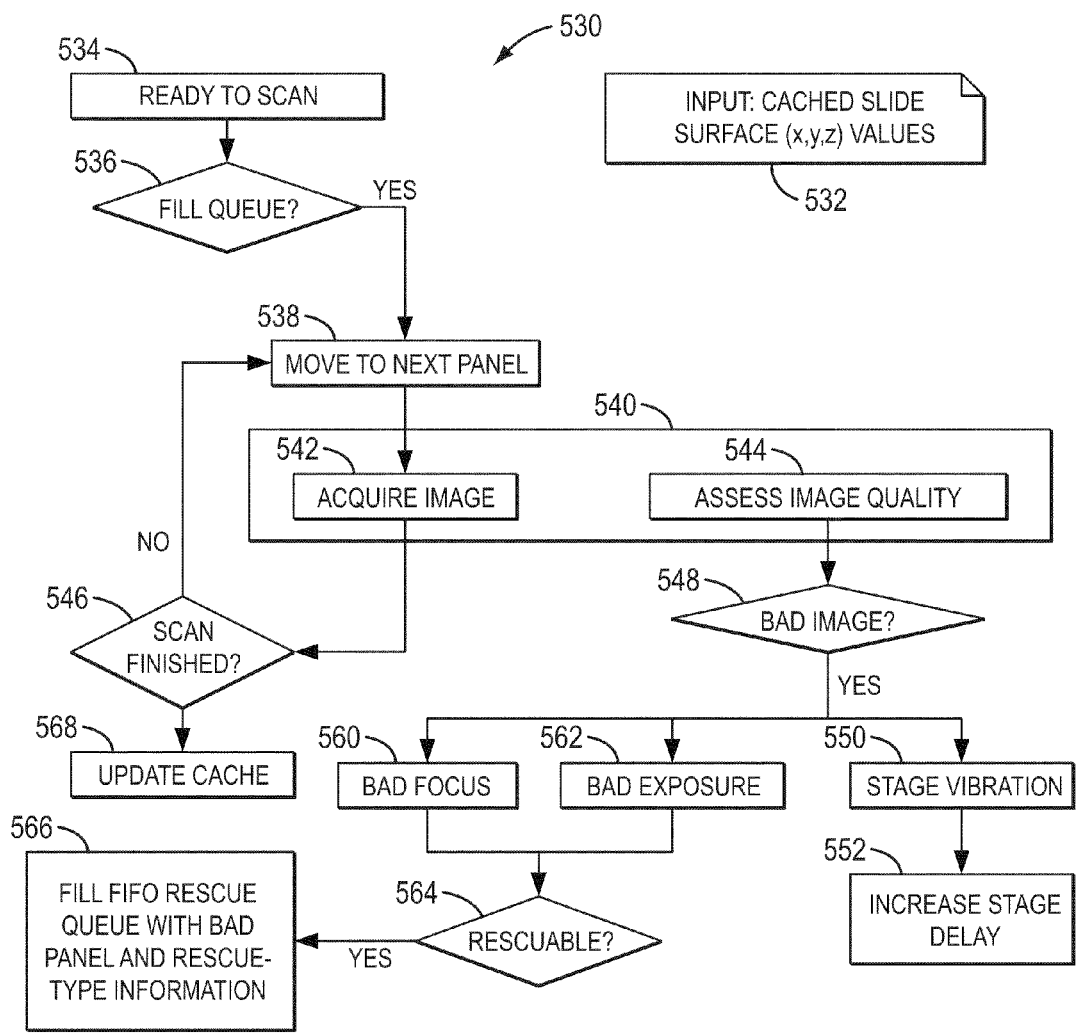
FIG. 28 shows an example process for determining whether a given panel of sequencing beads or particles should be rescued.

FIG. 28 shows an example process 530 that can identify and flag bad panels for rescue operations. As shown, information 532 about slide surface values can be made available to the process. In certain embodiments, such information can be in the form of cached information.

In a process block 534, the process 530 can be ready to scan (similar to the process block 516 in FIG. 27). In a decision block 536, the process 530 can determine whether a rescue queue should be filled. In certain embodiments, the queue can be filled if the queue is empty and/or if the queue (empty or not) is capable of receiving an entry. If the answer is "Yes," the process 530 can move or induce movement of the stage so as to allow imaging of the next panel in a process block 538. In certain embodiments, the process block 538 can be part of the "Stage Movement" portion of the scanning sequence described in reference to FIG. 20.

Once at the designated panel, the process 530 in a process block 540 can perform or induce performance of image acquisition (process block 542) and image quality assessment (process block 544). In certain embodiments, the process blocks 542 and 544 can be part of the "Camera Expose," "Transfer Image," and "Image Processing" portions of the scanning sequence described in reference to FIG. 20.

From the image acquisition process block 542, the process 530 in a decision block 546 can determine whether the scan is finished. If the answer is "No," the process 530 can proceed to the movement process block 538 described above.

From the image quality assessment block 544, the process 530 in a decision block 548 can determine whether the assessed image is a bad or non-optimal image. In certain embodiments, the decision block 548 can be part of the "Bad Image?" decision portion of the scanning sequence described in reference to FIG. 20. If the answer is "Yes," the process 530 can proceed to, for example, what to correct and/or how to correct a condition that may have contributed to the assessed image being bad.

In certain embodiments, the process 530 can determine whether the bad image is due to poor or non-optimal focus (process block 560), bad or non-optimal exposure (process block 562), or stage vibration (process block 550). For example, as described in reference to FIGS. 14 and 15, vibration condition can be detected based on the nature of elongations of the bead images. If the detected condition is stage vibration, the process 530 in a process block 552 can increase a stage delay so as to allow more settling down of the stage after movement.

If the detected condition is bad focus or bad exposure, the process 530 in a decision block 564 can determine whether the condition is rescuable. If the answer is "Yes," the process 530 in a process block 566 can fill the rescue queue with information such as bad panel identifier and the type of rescue to be performed. In certain embodiments, the rescue queue can be a first-in-first-out (FIFO) type queue.

In certain embodiments, the process and decision blocks 550, 552, 560, 562, 564, and 566 can be part of the "Rescue" portion of the scanning sequence described in reference to FIG. 20. In certain embodiments, the process 530 can be performed in real-time.

As previously described, the process 530 can continue scanning of the panels based on the decision block 546. In certain embodiments, the completion of the panel-scanning can also be determined by the decision block 546. Upon such completion, the process 530 can, in a process block 568, update the cached surface definition.

In certain embodiments, such updating of cached surface definition can include smoothing of the slide or substrate surface and removal of outlier points from the definition. For example, an input for such updating can include a list of (x, y, z) values of the panels and the corresponding image scores, a score threshold value, and a distance threshold value. Based on such input values, an output that includes a list of x, y, and new z values can be generated.

Figure 29:
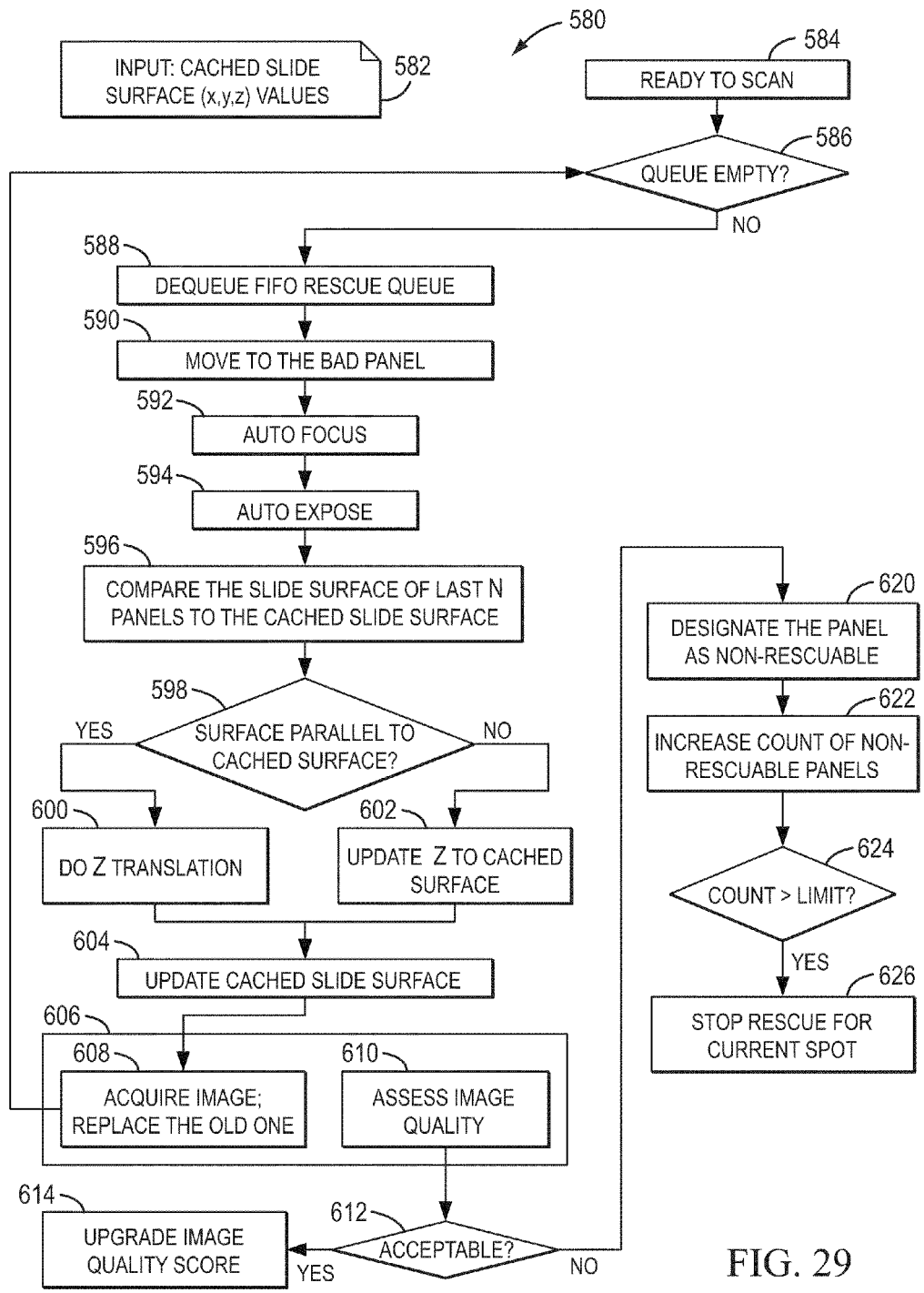
FIG. 29 shows an example process for performing the rescue based on the example process of FIG. 28.

A more detailed example for such updating can be as follows. A surface fit can be performed based on the input (x, y, z) values and using, for example, a cubic fit $z=ax3+by3+cx2y+dxy2+ex2+fy2+gxy+h$. For each (x, y, z), the z value can be replaced with a new z value if the corresponding image score is less than the score threshold value, or if its distance to the fit surface is greater than the distance threshold value. Upon completion of the comparison, the updated list of (x, y, z_new) can be returned. FIG. 29 shows an example process 580 that can perform rescue operations on bad panels that have been identified, such as those identified via the process 530 of FIG. 28. As shown, information 582 about slide or substrate surface values can be made available to the process. In certain embodiments, such information can be in the form of cached information. In certain embodiments, the cached slide surface information 582 can be the same as that of FIG. 28.

In a process block 584, the process 580 can be ready to scan (similar to the process block 516 in FIG. 27 and the process block 534 in FIG. 28). In a decision block 586, the process 580 can determine whether a rescue queue is empty. In certain embodiments, the rescue queue can be filled by the process 530 of FIG. 28. If the answer is "No," the process 580 in a process block 588 can dequeue an entry from the rescue queue. In certain embodiments, the queue can be a FIFO type queue.

Based on the dequeued information, the process 580 in a process block 590 can move or induce movement of the stage so as to allow re-imaging of the identified bad panel. In process blocks 592 and 594, auto focus and auto exposure can be performed for the image to be re-acquired.

In a process block 596, a comparison can be made between the slide or substrate surface as defined by last N panels to the corresponding slide or substrate surface as defined by the cached definition. In certain embodiments, the number N can be selected based on the total number of panels and a typical bad panel ratio, along with considerations for sampling time and the desired statistical confidence level. In certain embodiments, an odd integer can be selected for N so as to allow an easier computation of a median value. Such a comparison can provide additional information about how the bad image can be corrected, and also how the cached surface definition should or should not be updated. For example, the comparison can determine whether the slide or substrate surface as defined by the last N panels (which can be obtained from the auto focus settings at those panels) is approximately parallel to the surface defined by the cached definition. This determination can be made in a decision block 598. If they are parallel or approximately parallel, then an assumption can be made that a block of panels just scanned are bad, and that the surface defined by those panels should not be used to update the cache definition of the slide. Based on the assumption that the current cached definition is more correct, a correction can be made in the form of a Z translation of the stage to the cached Z value, as shown in a process block 600.

If the comparison shows that the two surfaces are not parallel, an assumption can be made that the current panel is bad, but not the block of panels. Based on such an assumption, the Z value obtained from the auto focus (process block 592) can be deemed to be more correct than the current cached value. Accordingly, the Z value of the cache definition at the current panel can be updated in a process block 602.

In a process block 604, cached definition of the slide or substrate surface can be updated appropriately based on the foregoing surface comparison.

In a process block 606, an image of the bad panel can be re-acquired (process block 608), and the re-acquired image can be assessed for quality (process block 610). From the image re-acquisition process block 608, the process 580 can query the rescue queue to see if it is empty. If the queue is empty, the process 580 can wait until the queue is not empty.

From the image assessment process block 610, the process 580 can, in a decision block 612, determine whether the quality of the re-acquired image is acceptable. If "Yes," the re-acquired image can be kept, and the image quality score can be upgraded in a process block 614. If "No," the current bad panel can be designated as non-rescuable in a process block 620.

In certain embodiments, the process 580 can keep track of the number of non-rescuable panels identified in the process block 620 for a given group of panels (e.g., the current spot having certain number of panels). Thus, in a process block 622, the number of non-rescuable panels can be incremented.

In a decision block 624, the process 580 can determine whether the current number of non-rescuable panels is greater than a selected limit. If "Yes," the process 580 in a process block 626 can stop further rescue operations for the current spot. Such tracking of non-rescuable panels and dynamically ceasing further rescue operations can improve the overall scanning time with reduced likelihood that remaining panels that are rescuable will not be rescued.

In certain embodiments, the example rescue queue filling process 530 of FIG. 28 and the example rescue process 580 of FIG. 29 can be performed generally concurrently. Some of the initializations process blocks, such as inputting of cached surface definition and readying the process for scanning can be shared.

As described herein, the example process 580 of FIG. 29 can dynamically cease further rescue operations in a given spot based on likelihood that certain fraction of the rest of the un-imaged panels will be un-rescuable. The threshold limit of accumulated non-rescuable panels (e.g., process and decision blocks 622 and 624 in FIG. 29) can be selected based on balancing of the need to not expend scanning time on un-rescuable panels and the need to not unnecessarily discard good panels.

In certain situations, the dynamic aborting of rescue operations in a given spot can be viewed as either saving scanning time (by not rescuing the rest of the panels) or having unnecessarily expended scanning time (by already having performed rescue operations on un-rescuable panels). Thus, in certain embodiments, it can be desirable to have a capability to determine whether a give spot of panels should have rescue mode turn on or off, prior to scanning that spot.

In certain embodiments, and as described in reference to FIGS. 28 and 29, detection of a bad image can trigger a rescue routine. In the example process 580 of FIG. 29, the rescue routine can include characterization of the slide surface for focus-related stage movements.

In certain embodiments, such surface characterization can be utilized to predict focusing on-the-fly so as to effectuate further stage movements at appropriate time. For example, a likely focusing surface can be predicted based on the current image assessment, and the stage can be moved further based on such prediction. In certain embodiments, such stage movement can be performed concurrently while some other tasks are being performed. Such a feature can reduce the image re-acquisition time, and thereby speed up the overall scanning process. Further, the likelihood of a subsequent image being assessed as having bad focus can be reduced, since the predicted focus will likely place the subsequent image closer to an ideal focus setting.

Figure 30:
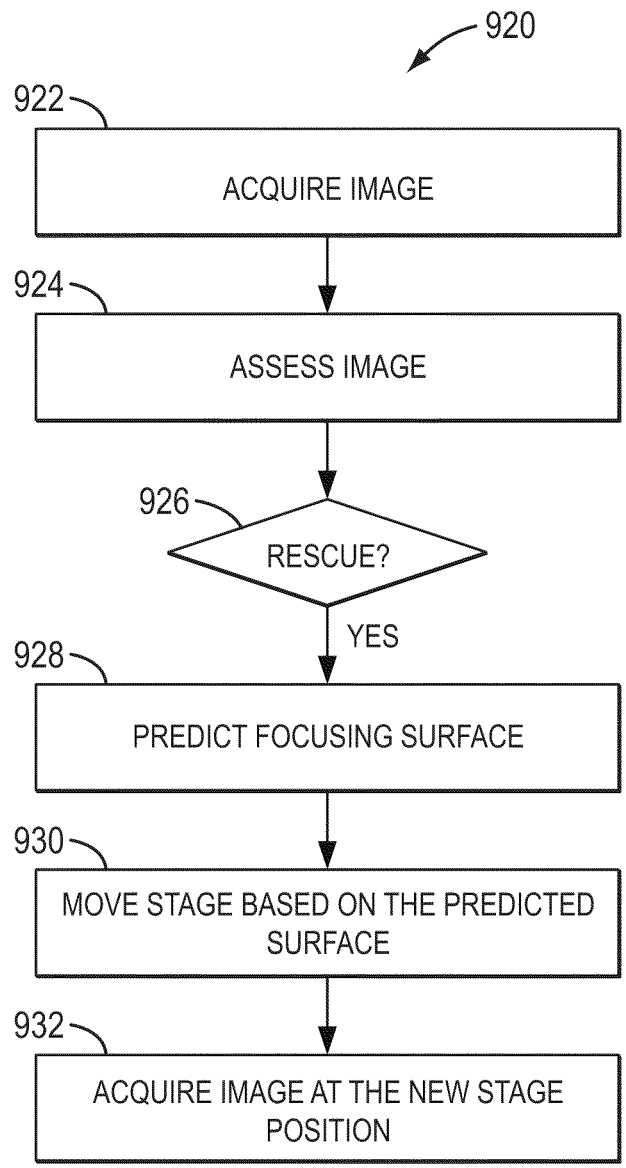
FIG. 30 shows that in certain embodiments, a detection of a bad image by the assessment can trigger a focusing surface correction routine to predict further stage movement, thereby reducing the likelihood of bad-focus images which in turn reduces the overall scanning time.

FIG. 30 shows a process 920 that can perform surface characterization and move the stage in a predicted manner based on such characterization. In a process block 922, an image can be acquired. In certain embodiments, such image acquisition can be part of a slide scanning process. In a process block 924, the acquired image can be assessed. If the assessment determines that the image should be rescued in a decision block 926, the process 920 can, in a process block 928, predict what an appropriate focusing surface setting will likely be. In certain embodiments, such prediction can be based on the comparison of the measured and cached surface definitions as described in reference to FIG. 29. In a process block 930, the process 920 can move or induce movement of the stage based on the predicted focusing surface. In certain embodiments, such stage movement can be performed prior to assessment of the next image. In a process block 932, the process 920 can acquire a new image at the new stage position (e.g., new z-position). In certain embodiments, such new image can be a re-acquired image of the bad image. In certain embodiments, such new image can be that of a new panel.

In certain embodiments, the process 920 can be performed in an on-the-fly manner. As such, the likelihood of the new image also being bad can be reduced since the stage is positioned at a likely better focus setting than what would be without the predictive movement. Further image acquisition or re-acquisition time can be reduced, since the slide movement (which can be a more time-consuming portion) is either completed or already in progress when the new image is to be acquired.

Figure 31:
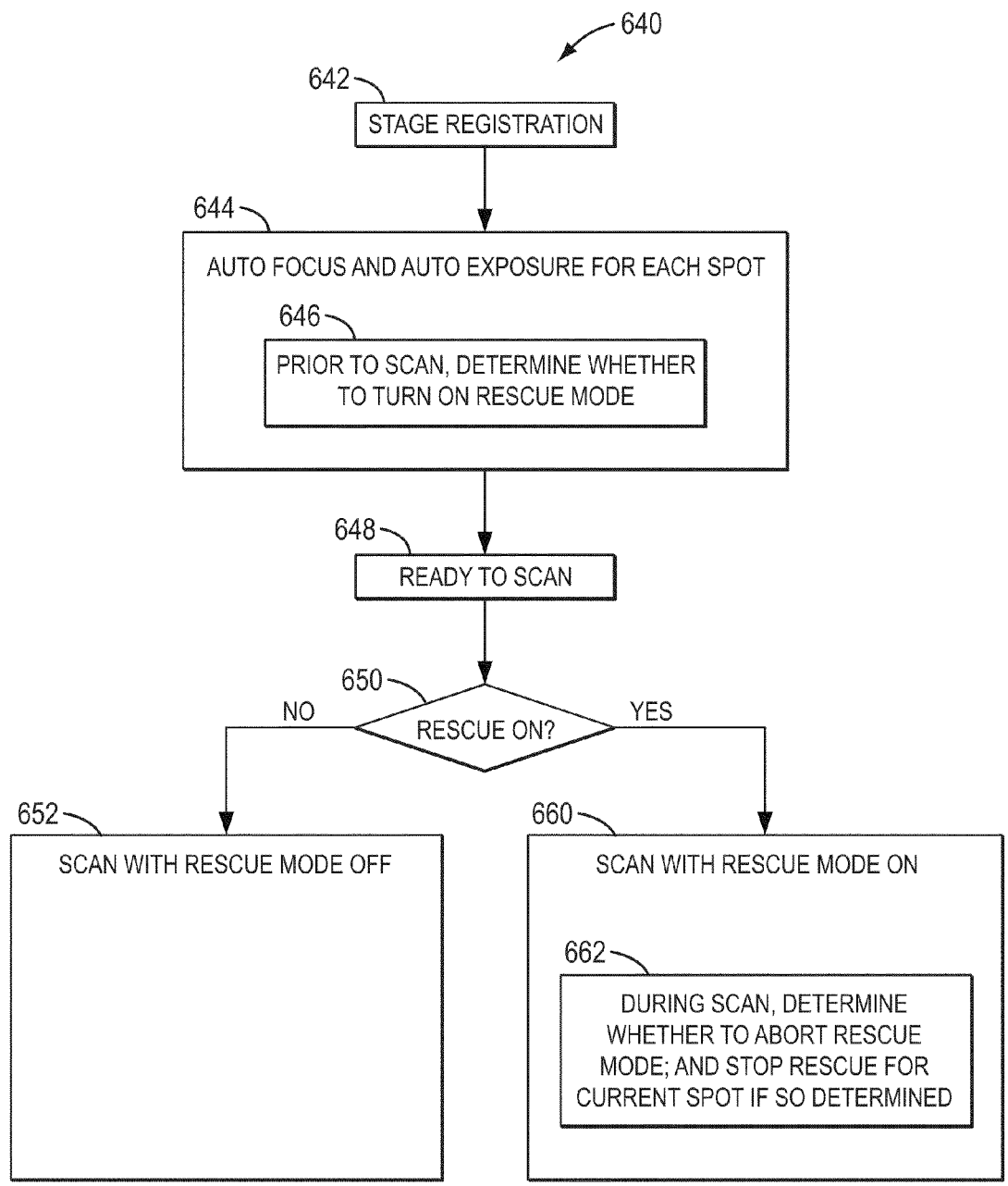
FIG. 31 shows that in certain embodiments, decisions can be made concerning rescuing a group of panels prior to scanning such panels, and/or during scanning of such panels, thereby allowing for a more efficient scan of the slide.

FIG. 31 shows an example process 640 that can determine whether to turn the rescue mode on or off prior to scanning of a spot. In a process block 642, stage registration can be performed. In a process block 644, auto focus and auto exposure settings can be obtained for each of the spots to be scanned. In certain embodiments, such focus and exposure settings can be the default settings for the panels in a given spot.

In certain embodiments, the process block 644 can include functionality (process block 646) where, prior to scanning of a given spot, a determination can be made as to whether to turn on the rescue mode. In certain embodiments, such determinations can be made for all of the spots to be scanned prior to the actual scanning of the spots.

In a process block 648, the process 640 can be configured to allow actual scanning of the spots and their respective panels.

In certain embodiments, the process 640 can determine whether a given spot should be scanned with rescue mode turned on in a decision block 650. If the answer is "No," scanning of the panels in that spot can be performed with rescue mode turned off in a process block 652. If the answer is "Yes," scanning of the panels in that spot can be performed with rescue mode turned on in a process block 660.

In certain embodiments, the process block 660, where scanning is being performed with rescue mode turned on, can include a process block 662 that can perform the dynamic determination to abort further rescue operations in a manner similar to that described in reference to FIG. 29.

Figure 32:
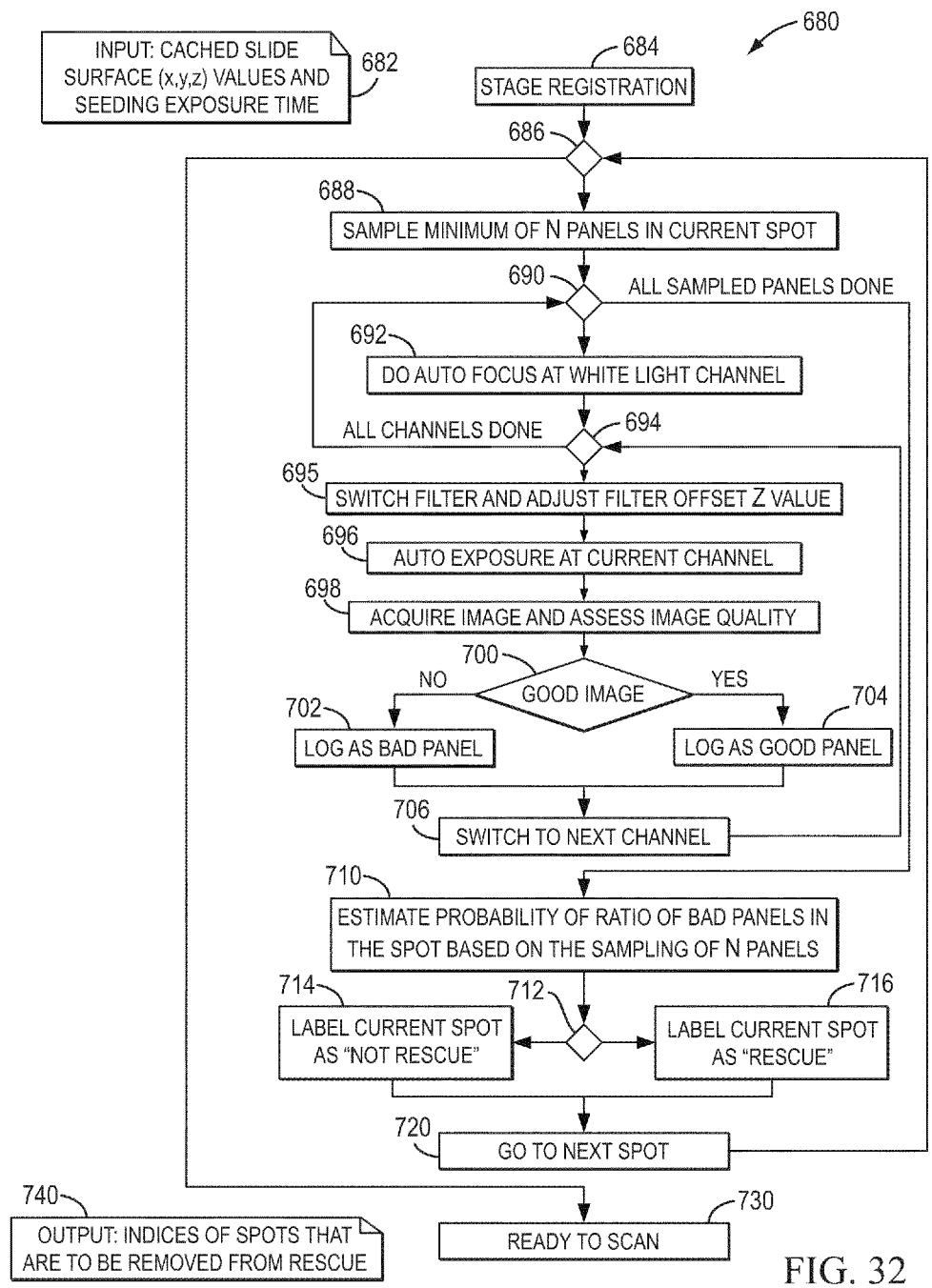
FIG. 32 shows an example process for determining whether rescue mode should be enabled for the group of panels prior to scanning of such panels.

FIG. 32 shows an example process 680 that can provide at least some of the functionality of the process block 646 in FIG. 31. In a process block 684, stage registration can be performed in a manner similar to those described herein. Similarly, cached definition (682) of slide or substrate surface can be made available to the process 680.

As shown, the process 680 can loop (686) through the spots to be scanned, and sample a minimum of N panels in the current spot in a process block 688. In certain embodiments, N can be based on a selected fraction of the total number of panels in the current spot. For example, approximately 1% of the panels can be sampled. Confidence levels and other statistical considerations are described herein in greater details.

In certain embodiments, assessment of the sampled panels can be based on images obtained from light from sources other than the fluorophores that are to be used during actual scanning. In certain embodiments, use of such light sources (such as white light sources) can be accommodated by the same assessment algorithms used for assessing the fluorescent emission sources (such as labeled probes associated with sequencing beads).

As shown in FIG. 32, auto focus, auto exposure, and image assessment can be performed for each of the N panels being sampled (loop 690). For the current panel, an auto focus setting can be obtained based on a white light or other source channel (process block 692). In certain embodiments, such a source channel can include light or electromagnetic radiation from an illumination source directed on the detector. In certain situations, such illumination can be attenuated via one or more filters such as a neutral density filter.

In certain embodiments, the process 680 can loop (between 694 and process block 706) through one or more fluorescent light channels (e.g., omission spectra associated with dyes such as, FAM, CY3, TXR, and CY5) to obtain and assess one or more images of the current panel. In a process block 695, the process 680 can switch filters appropriate for the current channel, and perform a z-position offset to account for the filter setting. In certain embodiments, such filter can be configured so as to prevent photo-bleaching of the sample by the current channel of light or illumination. In certain embodiments, the process 680 can be configured such that focusing is performed only for the channel corresponding to the current filter setting, thereby reducing the time spent on focusing. In certain embodiments, such filter offset may be needed due to slight differences in focusing positions between the white light channel and the fluorescent light channels. Typically, such differences can range between approximately 1 to 2 µm, and sometimes can be larger. For example, an offset between the white light channel and the FAM channel can be as large as about +2.77 µm. These offsets are typically constant for a given machine; but there can be machine-to-machine variations. Thus, the process block 695 can account for such focusing offsets.

In a process block 696, auto exposure can be obtained for the current channel. In a process block 698, an image of the panel can be acquired based on the current channel of light and assessed for image quality. In certain embodiments, the assessment can be similar to one or more methods described herein.

In a decision block 700, the process 680 can determine whether the acquired image of the sampled panel is a good image. If the answer is "Yes," the sampled panel can be logged as a good panel in a process block 704. If the answer is "No," the sampled panel can be logged as a bad panel in a process block 702. In certain embodiments, the image assessment process can be performed as a background task so as to reduce the overall sampling time. In a process block 706, the process 680 can switch to the next channel for the current panel.

Once all the sampled panels are processed, the process 680 in a process block 710 can estimate a probability of ratio of bad panels in the current spot based on the result of the assessment of the N sampled panels. Based on such an estimate, the process 680 can determine (in a decision block 712) whether the current spot should be labeled as a "do not rescue" spot (process block 714) or a "rescue" spot (process block 716).

In a process block 720, the process 680 can go to the next spot until all of the spots are sampled. Once all the spots are sampled, the process 680 can be ready to scan in a process block 730.

In certain embodiments, the process 680 can output information that includes indices of spots that are to be removed from rescue operations.

Figure 33:
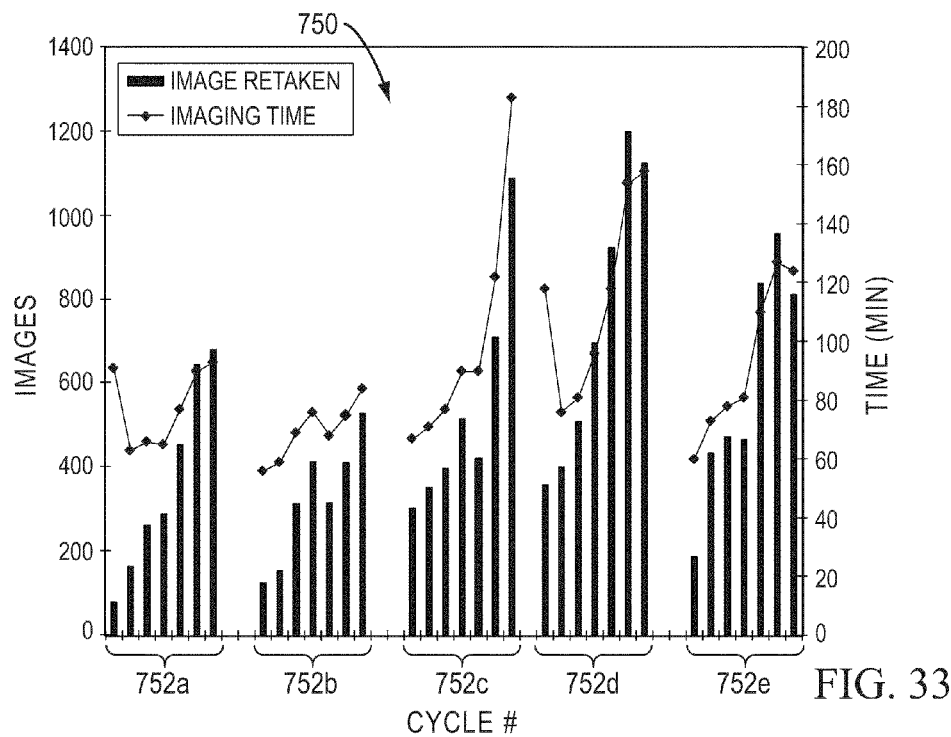
FIGS. 33 and 34 show how an imaging process can be made more efficient by optimizing, for example, how assessment is performed and how rescuing is implemented.
Figure 34:
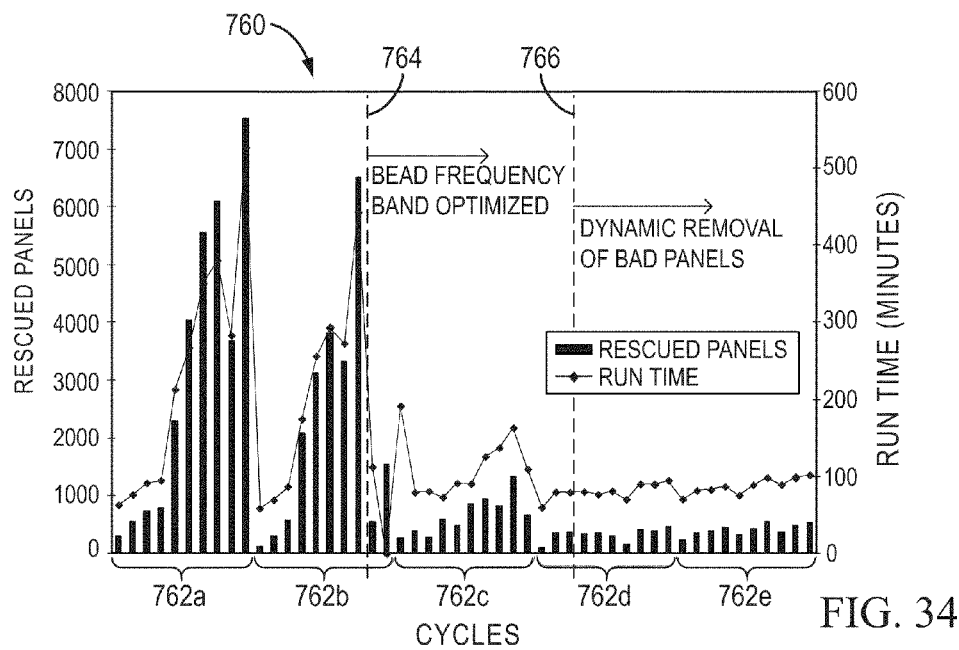

FIGS. 33 and 34 show a comparison of scanning performances (750 and 760) when bad panels are removed from rescue operations in a dynamic manner as described in reference to FIGS. 26-32. In FIG. 33 where rescue mode remains active throughout, groups of cycles (752a, 752b, etc.) of ligation are plotted on the horizontal axis. The vertical bars represent numbers of re-acquired images for each of the cycles, and the diamond data points represent time required to perform each of the cycles.

As shown, the number of re-acquired images generally increases significantly as the cycle number increases. As also shown, the time required to perform the cycles generally track the number of the re-acquired images, as expected since rescue operations require time.

In FIG. 34, where rescue mode is triggered dynamically for various spots (before and/or during scanning) starting at the vertical line 766, both the number of re-acquired images and the required scanning time are reduced dramatically, and remain at the relatively low values throughout the cycles.

In certain situations, such reduction in scanning time and the number of re-acquired images benefited from dynamic control of rescue modes can come at the expense of the risk of throwing away panels that could have been rescued. In certain embodiments, such a balancing of gains scanning speed versus possible loss in quality of the scan can be guided via various statistical considerations.

By way of a non-limiting example, consider the pre-scan determination of labeling the spots with rescue/no-rescue status as described in reference to FIGS. 31 and 32 (more particularly, in blocks 710 and 712). Suppose that a threshold is selected such that if there are more than T bad panels from a group of M panels, then the rescue mode will be turned off. If N panels are sampled and B panels are found to be bad, then the numbers N and B can be selected so as to provide a selected confidence level (e.g., 95%) with a spread using one of many known statistical models such as sampling models. In one of such sampling models, the N samples can be sampled in a random or substantially random manner. Such random sampling can be used to sample N panels during the pre-scan assessment of the spots.

In situations where a given spot is already being scanned and where the number of bad panels is being accumulated for a possible aborting of further rescue operations, it is likely that the sequence of panel scanning is not random. In such situations, whatever systematic sampling bias that may be introduced by such scanning sequence can be accounted for in known ways so as to provide a similar statistical guidance.

As described above in reference to FIG. 26, the monitoring component 500 can include components that determine whether to perform rescue operations and how to perform such rescue operations. FIGS. 27-34 relate to examples of such components.

As shown in FIG. 26, the monitoring component 500 can also include a component that relates to what and/or how to perform various embodiments of the assessment. As described herein, linear fitting of a one-dimensional representation of the two-dimensional FFT of the intensity distribution is an example of such an assessment process.

Figure 35:
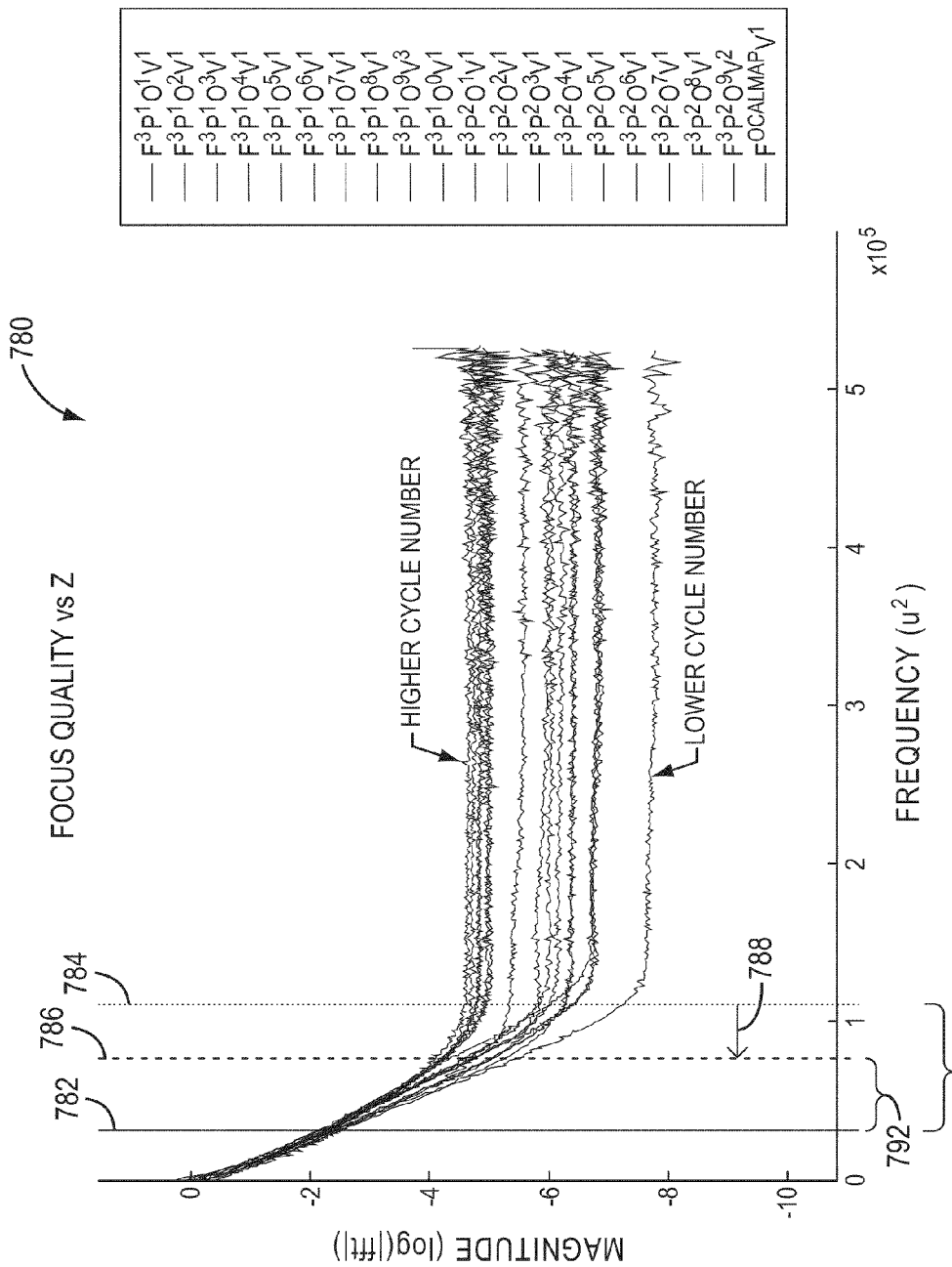
FIG. 35 shows that in certain situations, a manner in which assessment is performed can be modified in certain situations—for example, when sequencing beads or particles are subjected to multiple cycles of ligation.
Figure 36:
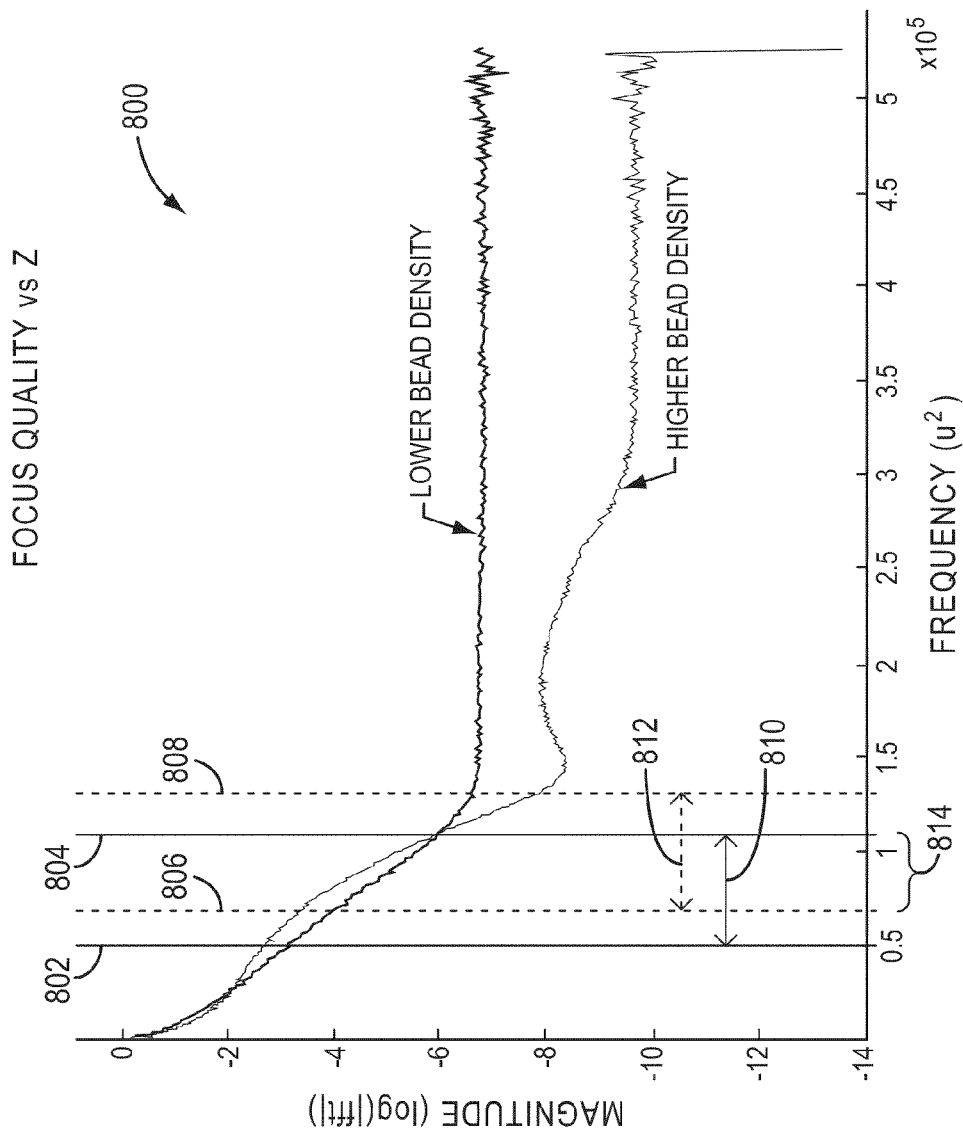
FIG. 36 shows that in certain situations, similar adjustment to the assessment configuration can be made to account for effects associated with an increase in density of the sequencing beads or particles.

FIGS. 34-36 show by non-limiting examples of how such assessment can be adjusted so as to enhance its effectiveness. As shown in FIG. 34, the vertical line 764 denotes a times during a scan when bead-frequency band optimization is turned on. As shown, such optimization has a significant effect in reducing the number of rescued panels and thus the scanning time.

An example of the bead-frequency band optimization is shown in FIG. 36, where a comparison of one-dimensional frequency spectra 800 are plotted—one for a lower bead density configuration and one for a higher bead density configuration. The higher bead density curve is shown to have an approximately linear portion in the range indicated by dashed lines 806 and 808; whereas the lower density curve is shown to have an approximately linear portion in the range indicated by solid lines 802 and 804.

As also shown, the upper limit (808) of the higher-density case is outside of the upper limit (810) of the lower-density case. Thus, when a situation is encountered where the bead density changes (e.g., from higher density to lower density), the frequency range for fitting can be adjusted so as to allow proper fit to a more proper range.

Adjusting the fitting range based on bead density is one of a number of examples of controlling how the assessment should be performed. FIG. 35 shows another non-limiting example related to a similar adjustment based on the cycle number of imaging situations such as those associated with multiple ligation or reaction cycles.

As described herein, scanning performance can degrade when the ligation or reaction cycle number increases. An example of such an effect is shown in FIG. 35 where a plurality of one-dimensional frequency spectra 780 are depicted. As shown, the upper curve corresponds to a higher cycle number case, and the lower curve corresponds to a lower cycle number case.

The lower cycle number case is shown to have a linear range 790 between the lines 782 and 784. The upper limit (784) of the linear range 790 is shown to exceed the linear portion of the higher cycle number case. Thus, as the cycle number increases, the range for fitting can be adjusted to accommodate the shift in linear portion of the spectrum. For example, the upper limit for the linear range can be adjusted (indicated by an arrow 788) from the line 784 to the line 786 so as to provide a range 792 that covers the linear portion of the higher cycle number case.

Although the above-disclosed embodiments have shown, described, and pointed out the fundamental novel features of the invention as applied to the above-disclosed embodiments, it should be understood that various omissions, substitutions, and changes in the form of the detail of the devices, systems, and/or methods shown may be made by those skilled in the art without departing from the scope of the invention. Consequently, the scope of the invention should not be limited to the foregoing description, but should be defined by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

What is claimed is:

1. A nucleic acid sequencing system, comprising:
a reaction chamber including a surface with one or more nucleic acid molecules disposed on said surface,
wherein said surface is populated with a plurality of labeled oligonucleotide probes arranged in a plurality of panels, and
wherein said plurality of oligonucleotide probes generate detectable signals and query the sequence of at least a portion of said one or more nucleic acid molecules;
an imaging system, including a focus component and an exposure component, configured to image said surface to detect said detectable signals and form images of said panels used in sequencing of said at least a portion of said one or more nucleic acid molecules;
a processor configured to assess the quality of said images based on a comparison of a measured signal distribution of a feature in said image with a reference signal distribution of the feature,
wherein said assessment indicates whether an image of a panel is non-optimal because the focus is outside of a preselected range, the image exposure is outside of a preselected range, or the image is elongated by reaction chamber vibration;
the processor configured to determine, based on said assessment, whether to perform a rescue operation for an image of a panel and how to perform said rescue operation, wherein said rescue operation includes reacquiring said panel image based on either a predicted focusing surface position or an increased delay after reaction chamber movement;

the processor configured to add a non-optimal panel to a rescue queue, based on said determination, with at least information identifying at least one non-optimal panel and a corresponding type of rescue to be performed for said at least one non-optimal panel; and the processor configured to correct for said at least one condition by instructing the imaging system to reacquire said panel images based on said rescue queue;

the processor configured to reassess the image quality of said reacquired images and designate each as either acceptable or non-rescuable.

2. The system of claim 1, wherein said measured signal distribution comprises a 2-dimensional intensity distribution of said feature.

3. The system of claim 2, wherein said reference signal distribution comprises a 2-dimensional Gaussian distribution.

4. The system of claim 3, wherein said measured signal distribution and reference signal distribution comprise fast Fourier transforms (FFT) of said 2-dimensional intensity distribution and 2-dimensional Gaussian distribution, respectively.

5. The system of claim 4, wherein said measured signal distribution and reference signal distribution comprise respective 1-dimensional representations of said FFTs of said 2-dimensional intensity distribution and 2-dimensional Gaussian distribution.

6. The system of claim 5, wherein said 1-dimensional representation comprises a distribution of a plurality of average values, each average value being calculated from values obtained from an isocentric circle about a peak value of the corresponding 2-dimensional distribution.

7. The system of claim 6, wherein said comparison comprises fitting of said 1-dimensional representation comprising FFTs of said measured signal distribution to said 1-dimensional representation comprising FFTs of said reference signal distribution.

8. The system of claim 7, wherein said 1-dimensional representations of measured signal distribution and reference signal distribution are linearized and used in a linear fitting.

9. The system of claim 8, wherein a correlation coefficient of said linear fitting provides an index of a quality of said image.

10. The system of claim 1, wherein said correction occurs in substantially real time.

11. The system of claim 1, wherein a quality value is generated and output to a user reflecting the assessment of focus quality.

12. The method of claim 1, wherein said assessment of said image occurs while another panel is imaged.

13. The method of claim 1, wherein said rescue operation is dynamically ceased when an accumulation of non-optimal panels is greater than a preselected limit.

14. The method of claim 1, wherein said surface is a bead.

15. The method of claim 1, wherein said surface is a slide.

* * * * *